(12) United States Patent
Willey et al.

(10) Patent No.: US 6,297,207 B1
(45) Date of Patent: *Oct. 2, 2001

(54) PHOTOCHEMICAL SINGLET OXYGEN GENERATIONS HAVING ENHANCED SINGLET OXYGEN YIELDS

(75) Inventors: Alan David Willey, Cincinnati, OH (US); Anthony Harriman, Bischheim (FR); Brian Jeffreys, Grimbergen; David William Ingram, Woluwe Saint-Lambergt, both of (BE)

(73) Assignee: Case Western Reserve University, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/355,157
(22) PCT Filed: Jan. 22, 1998
(86) PCT No.: PCT/US98/00223
   § 371 Date: Jul. 23, 1999
   § 102(e) Date: Jul. 23, 1999
(87) PCT Pub. No.: WO98/32825
   PCT Pub. Date: Jul. 30, 1998

Related U.S. Application Data
(60) Provisional application No. 60/035,904, filed on Jan. 24, 1997.

(51) Int. Cl.[7] ............................. C11D 3/395; C11D 9/08
(52) U.S. Cl. ................... 510/301; 540/128; 540/139; 540/140
(58) Field of Search ........................... 510/301; 540/140, 540/128, 139

(56) References Cited

U.S. PATENT DOCUMENTS

| | | | |
|---|---|---|---|
| 3,094,536 | 6/1963 | Kenney et al. | 260/314.5 |
| 3,927,967 | 12/1975 | Speakman | 8/103 |
| 4,033,718 | 7/1977 | Holcombe et al. | 8/103 |
| 4,166,718 | 9/1979 | Reinert et al. | 8/111 |
| 4,240,920 | 12/1980 | de Luque | 252/99 |
| 4,255,273 | 3/1981 | Sakkab | 252/102 |
| 4,256,597 | 3/1981 | Sakkab | 252/99 |
| 4,318,883 | 3/1982 | Polony et al. | 422/22 |
| 4,368,053 | 1/1983 | Eckhardt et al. | 8/102 |
| 4,497,741 | 2/1985 | Hölzle et al. | 260/245.77 |
| 4,648,992 | 3/1987 | Graf et al. | 540/124 |
| 5,916,481 | * 6/1999 | Willey | 252/186.21 |

FOREIGN PATENT DOCUMENTS

| | | | |
|---|---|---|---|
| 0 285 965 | 10/1988 | (EP) | C09B/67/22 |
| 0 381 211 | 8/1990 | (EP) | G11B/7/24 |
| 0 484 027 | 5/1992 | (EP) | C09B/47/04 |
| 1372035 | 10/1974 | (GB) | . |
| 1408144 | 1/1975 | (GB) | . |
| 2159516 | 12/1985 | (GB) | C09B/47/04 |
| 6-73397 | 3/1994 | (JP) | C11D/3/395 |
| WO 91/18006 | 11/1991 | (WO) | C07J/43/00 |

OTHER PUBLICATIONS

Brasseur, N., et al., "Synthesis and Photodynamic Activities of Silicon 2,3–Naphthalocyanine Derivatives", J. Med. Chem., vol. 37, p. 415–420 (1994).

Cook, M.J. et al., "Octa–alkoxy Phthalocyanine and Naphthalocyanine Dertivatives: Dyes with Q–band Absorption in the Far Red or Near Infrared" J. Chem. Soc., Perkin Trans., vol. 1., p. 2453–2458 (1988).

Esposito, J.N. et al., "Teh Synthesis and Physical Properties of Some Organo– and Organosiloxysilicon Phthalocyanines", Inorg. Chem., vol. 5, No. 11, pp. 1979–1984 (Nov. 1966).

Ford, W.E. et al., "Synthesis and Photochemical Properties of Aluminum, Gallium, Silicon, and Tin Naphthalocyanines", Inorg. Chem., vol. 31, p. 3371–3377 (1992).

Hayashida, S., et al., "Effect of axial Substituents on the Aggregate of Silicon Naphthalocyanine in the Vacuum Deposited Thin Films", Chem. Lett., pp. 2137–2140 (1990).

Joyner, R.D. et al, "Phthalocyaninosilicon Compounds", Inorg. Chem., vol. 1, No. 2, pp. 236–238 (May 1962).

Kroenke, W.E. et al., "The Infrared Spectra of Some Tin and Lead Phthalocyanines", Inorg. Chem., vol. 3, No. 5, pp. 696–698 (May 1964).

Lowery, M.H. et al., "Dichloro(phthalocyanino)silicon", Inorg. Chem., vol. 4, p. 128 (1965).

Moyer, T. J., et al., "Iodine Doped $(SiNcO)_n$–A new Conducting Polymer", Polymer Preps, vol. 25, p. 234–235 (1986).

Rafaeloff, R., et al., "New Group Iv Phthalocyanines", J. Inorg. Nucl. Chem., vol. 28, pp. 899–902 (1966)

Wen, T–C., et al., "Synthesis and Photoproperties of Silicon Phthalocyanines and Silicon Naphthalocyanines", J. Chin. Chem. Soc., vol. 40, pp. 141–147 (1993).

Wheeler, B.L. et al., "a Silicon Phthalocyanine and a Silicon Naphthalocyanine; Synthesis, Electrochemistry, and Electrogenerated Chemiluminescence" J. Am. Chem. Soc., vol. 106, p. 7404–7410 (1984).

Witkiewic, Z. et al., "Properties of Octamethoxyphthalocyanines I. On their syntheses, electrical conductivity, and Catalytic activity", Material Science, vol. 11, No. 1–2, pp. 39–45 (1976).

* cited by examiner

Primary Examiner—John Hardee
(74) Attorney, Agent, or Firm—Fay Sharpe Fagan Minnich & McKee, LLP

(57) ABSTRACT

The invention relates to photochemical singlet oxygen generators useful as bleaching agents or anti-microbial agents in laundry detergent compositions or in hard surface cleaning compositions. The singlet oxygen generators described herein have enhanced singlet oxygen generation due to aromatic moieties teed to the molecules, said aromatic moieties absorbing ultra violet radiation then re-emitting the radiation as fluorescence at a wavelength absorbable by the singlet oxygen producing photosensitizer unit. The increase in the number of photons having an absorbable wavelength provides an increase in the production of singlet oxygen.

15 Claims, No Drawings

PHOTOCHEMICAL SINGLET OXYGEN GENERATIONS HAVING ENHANCED SINGLET OXYGEN YIELDS

This Applications Claims priority from U.S. Provisional Applications No. 60/035,904 filed Jan. 24, 1997.

FIELD OF THE INVENTION

The present invention relates to photochemical singlet oxygen generators having a photon harvester moiety which enhances the singlet oxygen yield of the generator without adversely affecting the remaining properties of the molecule. The photochemical singlet oxygen generators described herein are useful in laundry detergent compositions or hard surface cleaning compositions as bleaching agents or anti-microbial agents. The present invention also relates to methods for bleaching fabrics and cleaning hard surfaces with the photochemical singlet oxygen generators.

BACKGROUND OF THE INVENTION

It is known that certain water soluble phthalocyanine and naphtalocyanine, mixed cyanine and metallocyanine compounds can be used as photobleaching and anti-microbial agents. Phthalocyanines and naphthalocyanines or their metal complexes can form "singlet oxygen".

Singlet oxygen can be formed by chemical as well as photochemical processes. Singlet oxygen is a highly oxidative species capable of reacting with substances, for example, with stains on a fabric to bleach them to a colorless and usually water-soluble state. There are many examples of phthalocyanines and naphthalocyanines photobleaches, the most common being the zinc and aluminum phthalocyanines. In the literature the term "photosensitizer" is often used instead of "photoactivator" and may therefore be considered as standing equally well for the latter term used throughout this specification The prior art teaches phthalocyanine and naphthalocyanine compounds having the general structure

where Me is a tnansition or non-transition metal, (Sens.) is a phthalocyanine or naphthalocyanine ring which, when combined with a suitable Me unit, is capable of undergoing photosensitization of oxygen molecules, R units are substituent groups which are bonded to the photosensitization ring units (Sens.) to enhance the solubility or photochemical properties of the molecule, and Y units are substituents associated with the metal atom, for example, anions to provide electronic neutrality.

It has been a task of formulators of photobleaches to modify the properties of the (Sens.) unit of the molecule to increase the quantum efficiency and/or the water solubility. Typically this has been accomplished by substitution on the photochemical (Sens.) ring. However, substituents that improve one property may have a negative effect on the other. Consequently it has proven difficult to provide photobleaches which are water soluble and efficient.

Surprisingly, it has been found that the compounds of the present invention allow formulators to increase the photo-efficiency of the singlet oxygen generators while being able to maintain the other parameters of the molecule. In addition, the solubility of the photochemical singlet oxygen generator can be modified without producing an undesired effect in the photophysics of the molecule. This ability to delineate and selectively modify the key structural elements contributing to the target properties of the molecule allows the formulator to proceed without having to rely upon a "hit and miss" stratagem.

The present invention provides a means by which an effective photosensitizer can have its efficiency increased without risking a concomitant loss of other desired properties inter alia solubility or color. This task is achieved by attaching a photon "harvester" moiety to the singlet oxygen generator. This harvester absorbs ultra violet light and transfers the energy to the photosensitizer portion of the molecule via a process known to those of skill in the art as "Foster Energy Transfer". This harvester group must be within a critical distance to facilitate this energy transfer. This energy transfer acts to increase the effective number of photons absorbed by the photosensitizer unit and, as photons are "consumed" in producing singlet oxygen, an increase therefore in singlet oxygen generation.

It is therefore an object of the present invention to provide photochemical singlet oxygen generators which serve as photobleaches and photodisinfectants and which have a higher efficiency in producing singlet oxygen. It is a further object of the present invention to provide photobleaching compositions suitable for use as laundry detergent bleaching compositions.

It is a yet further object of the present invention to provide enhanced photobleaching hard surface cleaning compositions for non-porous hard surfaces, inter alia, Formica®, ceramic tile, glass, or for porous hard surfaces such as concrete or wood.

It is a still further object of the present invention is to provide a method for bleaching fabric with laundry compositions comprising the photobleaching compounds of the present invention It is yet still a further object of the present invention is to provide a method for cleaning hard surfaces with the photobleaching compounds of the present invention.

BACKGROUND ART

Various patent documents relate to photochemical bleaching or to the use of cyanine compounds as well as their formulation and synthesis. See for example U.S. Pat. No. 3,094,536 issued Jun. 18, 1963; U.S. Pat. No. 3,927,967 issued Dec. 23, 1975; U.S. Pat. No. 4,033,718 issued Jul. 5, 1977; U.S. Pat. No. 4,166,718 issued Sep. 4, 1979; U.S. Pat. No. 4,240,920 issued Dec. 23, 1980; U.S. Pat. No. 4,255,273 issued Mar. 10, 1981; U.S. Pat. No. 4,256,597 issued Mar. 17, 1981; U.S. Pat. No. 4,318,883 issued Mar. 9, 1982; U.S. Pat. No. 4,368,053 issued Jan. 11, 1983; U.S. Pat. No. 4,497,741 issued Feb. 5, 1985; U.S. Pat. No. 4,648,992 issued Mar. 10, 1987; and U.K. Pat. App. 1,372,035 published Oct. 30, 1974; U.K Pat. App. 1,408,144 published Oct. 1, 1975; U.K. Pat App. 2,159,516 published Dec. 4, 1985; E.P. 285,965 A2; E.P. 381,211 A2 published Aug. 8, 1990; E.P. 484,027 A1 published May 6, 1992; WO 91/18006 published Nov. 28, 1991 and Japanese Kokai 06-73397 Derwent Abst. No. (94128933) published Mar. 15, 1994.

In addition to the above cited patent publications, other references describing the synthesis, preparation and properties of cyanines, incorporated herein also by reference; *Phthalocyanines: Properties and Applications,* Leznoff, C. C. and Lever A. B. P. (Eds), VCH, 1989; *Infrared Absorbing Dyes,* Matsuoka, M. (Ed), Plenum, 1990; *Inorg. Chem.,*

Lowery, M. J. et al., 4, pg. 128, (1965); *Inorg. Chem.* Joyner R. D. et al., 1, pg. 236, (1962); *Inorg. Chem.*, Kroenke, W. E. et al., 3, 696, 1964; *Inorg. Chem.* Esposito, J. N. et al., 5, pg.1979, (1966); *J. Am. Chem. Soc.* Wheeler, B. L. et al., 106, pg. 7404, (1984); *Inorg. Chem.* Ford, W. E, et al., 31, pg. 3371, (1992); *Material Science,* Witkiewicz, Z. et al., 11, pg. 39, (1978); *J. Chem. Soc.* Perkin Trans. I, Cook, M. J., et al., pg. 2453, (1988); *J. Chin. Chem.* Soc., 40, pg. 141, (1993); *J. Inorg. Nucl Chem.,* 28, pg. 899, (1966); *Polymer Preps,* 25, pg. 234, (1986); Chem. Lett., 2137, (1990); *J. Med. Chem.,* 37, pg. 415, (1994).

SUMMARY OF THE INVENTION

The present invention relates to singlet oxygen generators useful as a bleaching agent or disinfectant in laundry detergent compositions and hard surface cleaning compositions, said singlet oxygen generators having the formula:

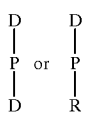

wherein P is a photosensitizer unit; R is an axial moiety which mediates the solubility or substantivity of the singlet oxygen generator, and D is a unit which increases the efficiency of singlet oxygen production, said unit having the formula

or

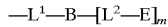

wherein E is an aromatic unit, provided said E aromatic unit:
 a) absorbs ultra violet radiation at a wavelength of from about 200 nm to about 400 nm;
 b) has an extinction coefficient of at least about 100; and
 c) has a fluorescence spectrum which overlaps an absorption band of said photosensitizer unit;
B is a branching unit; and $L^1$ and $L^2$ are linking units, provided said linking units when taken together with said B unit comprise a total of at least 20 continuous covalent bonds from said P unit to said E units; m is from 2 to 4.

All percentages, ratios and proportions herein are by weight, unless otherwise specified. All temperatures are in degrees Celsius (°C.) unless otherwise specified. All documents cited are in relevant part, incorporated herein by reference.

DETAILED DESCRIPTION OF THE INVENTION

The present invention relates to photochemical singlet oxygen generators which have an enhanced chromophoric groups. This increase in photoefficiency is due to the presence of a photon "harvester" moiety which is capable of broadening the electromagnetic radiation utilized by the photosensitizing unit in the production of singlet oxygen The present invention also relates to cleaning compositions which comprise the photochemical singlet oxygen generators of the present invention. Laundry detergent compositions according to the present invention comprise:
 a) at least about 0.1%, preferably from about 0.1% to about 30%, more preferably from about 1% to about 30%, most preferably from about 5% to about 20% by weight, of a detersive surfactant wherein the detersive surfactant is selected from the group consisting of anionic, cationic, nonionic, zwitterionic, ampholytic surfactants, and mixtures thereof;
 b) at least about 0.001 ppm, preferably from about 0.01 to about 10000 ppm, more preferably from about 0.1 to about 5000 ppm, most preferably form about 10 to about 1000 ppm, of a singlet oxygen generator having the formula:

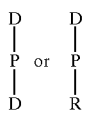

wherein P is a photosensitizer unit; R is optionally an axial moiety which mediates the solubility or substantivity of the singlet oxygen generator; and D is a unit which increases the efficiency of singlet oxygen production, said unit having the formula

or

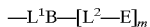

wherein E is an aromatic unit, provided said E aromatic unit:
 i) absorbs ultra violet radiation at a wavelength of from about 200 nm to about 400 nm;
 ii) has an extinction coefficient of at least about 100; and
 iii) has a fluorescence spectrum which overlaps an absorption band of said photosensitizer unit;
B is a branching unit; and $L^1$ and $L^2$ are linking units, provided said linking units when taken together with said B unit comprise a total of at least 20 continuous covalent bonds from said P unit to said E units; m is from 2 to 4; and
 c) the balance carriers and adjunct ingredients, said adjunct ingredients are selected from the group consisting of buffers, builders, chelants, filler salts, soil release agents, dispersants, enzymes, enzyme boosters, perfumes, thickeners, abrasives, solvents, clays, and mixtures thereof Photosensitizing Units, P The photosensitizers of the present invention suitable for use as photobleaches and photodisinfectants comprise cyanine rings as well as hybrid cyanine rings. The cyanine rings are those formed from four identical aromatic units, for example, phthalocyanines and naphthalocyanines. The hybrid rings are formed by chemically reacting together at least two different aromatic monomer units capable of forming a cyanine ring. Typically, cyanine rings are defined by the type of aromatic monomer unit used to synthesize the target macrocyclic ring, for example, phthalocyanines are formed from derivatives of benzene, naphthalocyanines are formed from derivatives of naphthalene, etc.

The cyanine rings of the present invention have the general formula

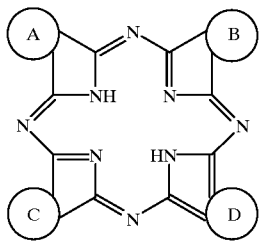

wherein A, B, C, and D represent aromatic rings. For the purposes of the present invention these aromatic rings are preferably substituted or unsubstituted benzene, 1,2-naphthylene, 2,3-naphthalene, anthracene, and phenanthrene. However, this list is not meant to be inclusive or exclusive of any other aromatic ring capable of insertion into the cyanine ring including aromatic heterocyclic rings inter alia quinolines or isoquinolines.

For the purpose of further illustrating the formation of hybrid cyanine rings useful for preparing the singlet oxygen generators of present invention, the scheme below depicts the expected mixture of cyanine rings obtained when the cyanine ring forming monomers, 1,6dimethoxy-3,4-dicyanobenzene and 1,6-dibromo-3,4-dicyanobenzene, are reacted together under suitable conditions.

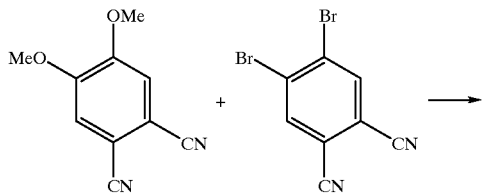

Reacted together under suitable conditions yield:

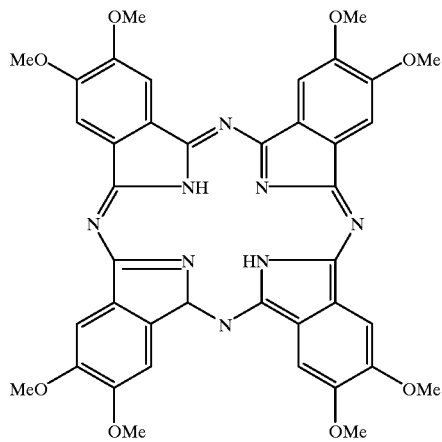

I

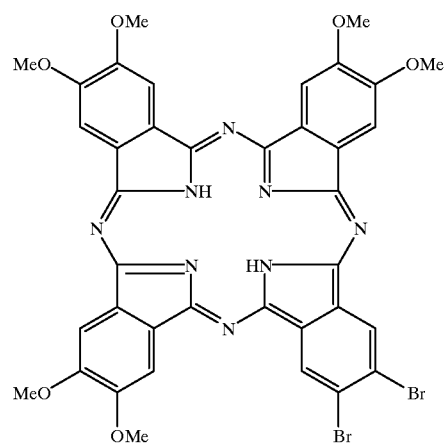

II

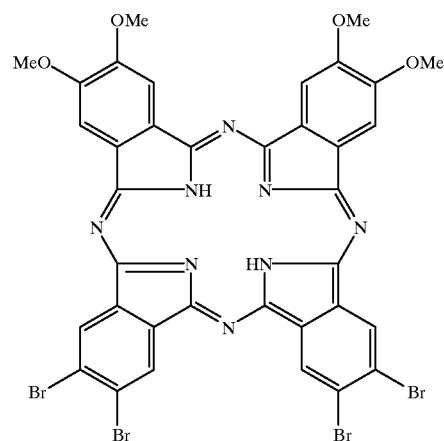

III

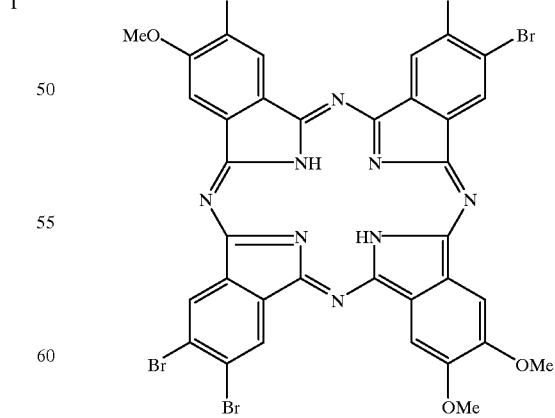

IV

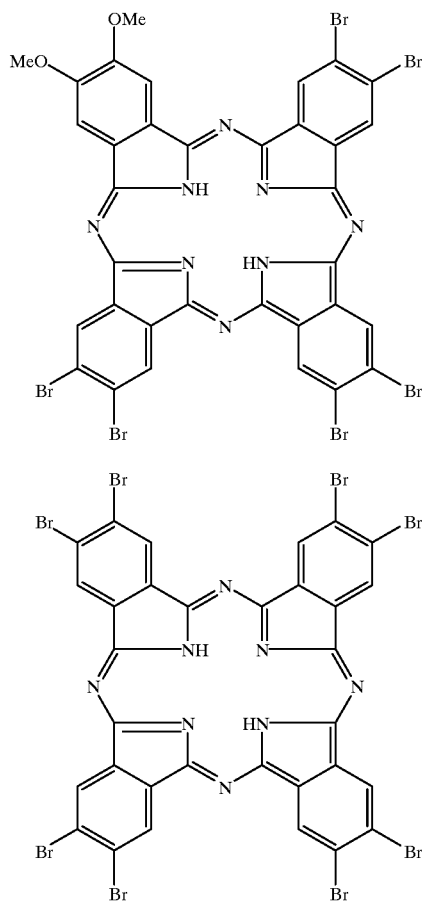
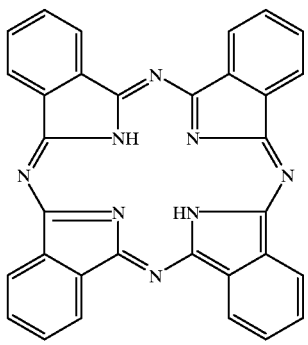
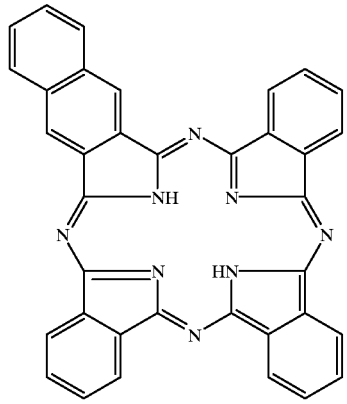
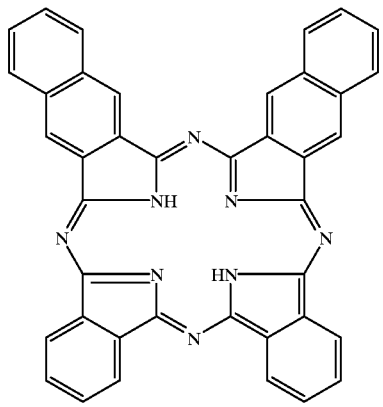
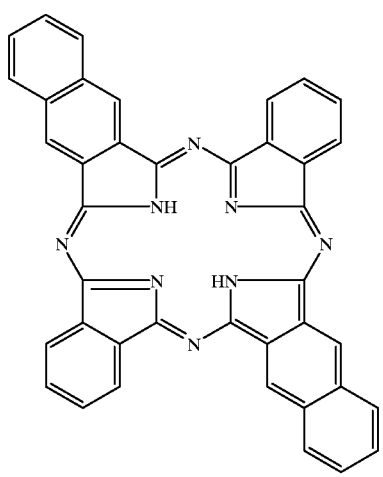
Other examples include but are not limited to the reaction of orthodicyanobenzene and 2,3dicyanonaphthalene as shown below
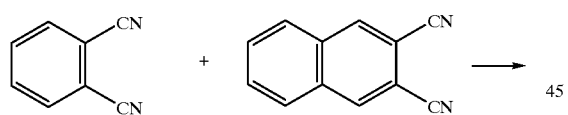
or the reaction of the corresponding phthalimidines as shown below
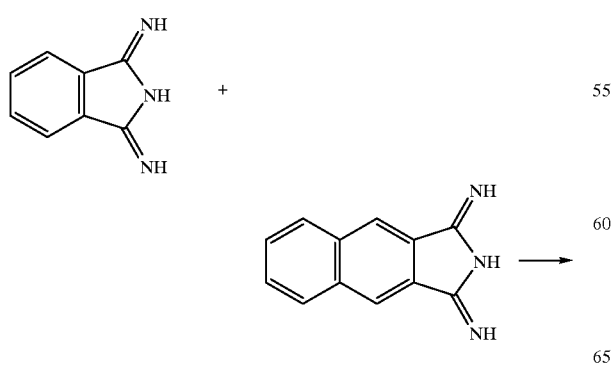
to yield the mixture of hybrid cyanines I–VI shown below.

V

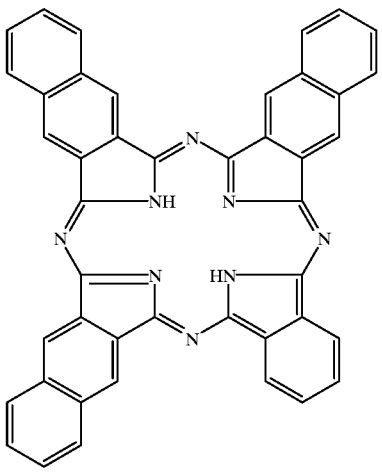

VI

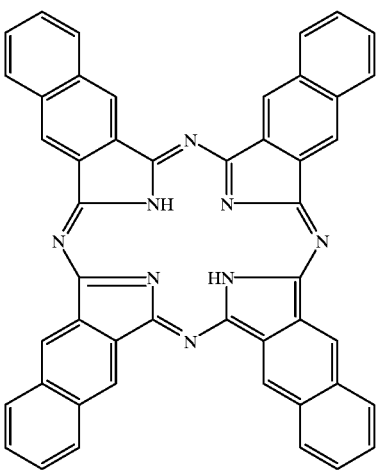

For the purposes of the present invention ring components derived from substituted and unsubstituted benzene can be written in either of two equivalent resonance formulas:

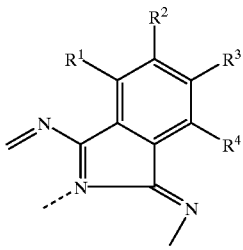

wherein $R^1$, $R^2$, $R^3$ and $R^4$ are each independently selected from the substituents described herein below.

For the purposes of the present invention ring components derived from substituted and unsubstituted 2,3-naphthylene can be written in either of two equivalent resonance formulas:

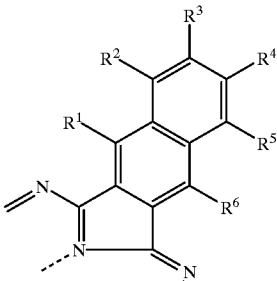

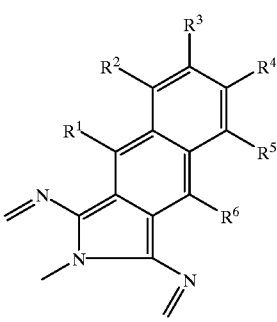

wherein $R^1$, $R^2$, $R^3$, $R^4$, $R^5$, and $R^6$ are independently selected from the substituents described herein below.

For the purposes of the present invention ring components derived from substituted and unsubstituted 1,2-naphthylene can be written in either of two equivalent resonance formulas:

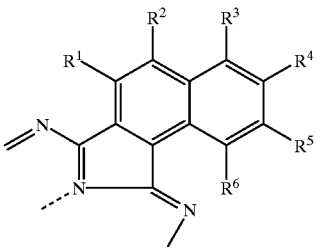

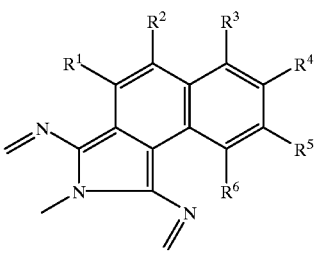

wherein $R^1$, $R^2$, $R^3$, $R^4$, $R^5$, and $R^6$ units are independently selected from the substituents listed herein below.

For the purposes of the present invention ring components derived from substituted and unsubstituted 2,3-naphthylene can be written in either of two equivalent resonance formulas:

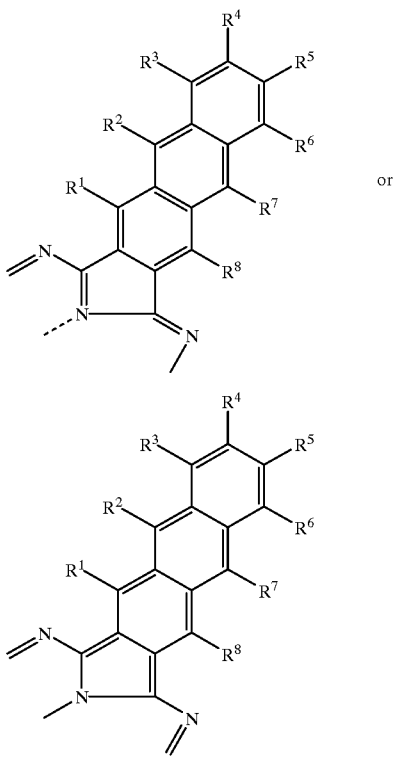

or wherein $R^1$, $R^2$, $R^3$, $R^4$, $R^5$, $R^6$, $R^7$, and $R^8$ units are independently selected from the substituents described herein below.

For the purposes of the present invention ring components derived from substituted and unsubstituted phenanthrene can be written in either of two equivalent resonance formulas:

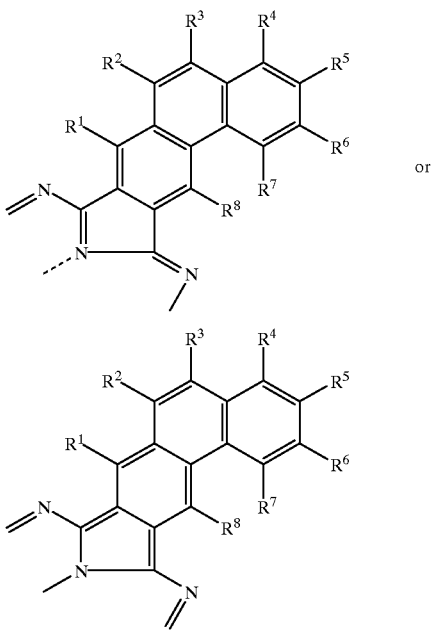

wherein $R^1$, $R^2$, $R^3$, $R^4$, $R^5$, $R^6$, $R^7$, and $R^8$ units are independently selected from the substituents described herein below.

Each $R^1$, $R^2$, $R^3$, $R^4$, $R^5$, $R^6$, $R^7$, and $R^8$ unit is independently:

a) hydrogen,
b) halogen;
c) hydroxyl;
d) $C_1$–$C_{22}$ alkyl, $C_3$–$C_{22}$ branched alkyl, $C_2$–$C_{22}$ alkenyl, $C_3$–$C_{22}$ branched alkenyl;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl;
f) polyhydroxyl substituted $C_3$–$C_{22}$ alkyl;
g) $C_1$–$C_{22}$ alkoxy, preferably $C_1$–$C_4$ alkoxy, more preferred methoxy;
h) branched alkoxy having the formula

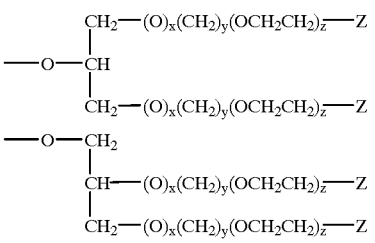

wherein Z is hydrogen, hydroxyl, $C_1$–$C_{30}$ linear alkyl, $C_1$–$C_{30}$ branched alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, and mixtures thereof; M is a water soluble cation in sufficient amount to satisfy charge balance; x is 0 or 1, each y independently has the value from 0 to 6, preferably from 0 to 6; each z independently has the value from 0 to 100, preferably from 0 to about 10, more preferably from 0 to about 3;

i) substituted aryl, and unsubstituted aryl having the formula:

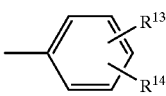

wherein $R^{13}$ and $R^{14}$ are independently selected from the group consisting of hydrogen, $C_1$–$C_6$ alkyl, $C_3$–$C_6$ alkenyl, $C_1$–$C_6$ alkoxy, $C_3$–$C_6$ branched alkoxy, halogen, —$CO_2^-M^+$, —$SO3^-M^+$, —$OSO_3^-M^+$, —$N(R^{15})_2$, and —$N^+(R^{15})_3X^-$ wherein each $R^{15}$ is independently hydrogen or $C_1$–$C_4$ alkyl; and mixtures thereof, preferably hydrogen $C_1$–$C_6$ alkyl, —$CO_2^-M^+$, —$SO_3^-M^+$, —$SO_3^-M^+$, and mixtures thereof, more preferably $R^{13}$ or $R^{14}$ is hydrogen and the other moiety is $C_1$–$C_6$ alkyl; wherein M is a water soluble cation and X is a water soluble anion.

j) substituted alkylenearyl and unsubstituted alkylenearyl having the formula:

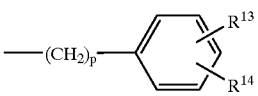

wherein $R^{13}$ and $R^{14}$ are as defined above, p is from 1 to about 10.

k) substituted aryloxy and unsubstituted aryloxy having the formula:

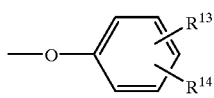

wherein $R^{13}$ and $R^{14}$ are as defined above.

l) substituted alkyleneoxyaryl and unsubstituted alkyleneoxyaryl units are defined as moieties having the formula:

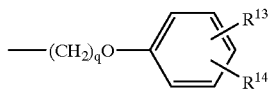

wherein $R^{13}$ and $R^{14}$ are as defined above, q is from 0 to about 10.

m) substituted oxyalkylenearyl and unsubstituted oxyalkylenearyl having the formula:

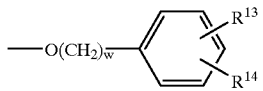

wherein $R^{13}$ and $R^{14}$ are as defined above, w is from about 1 to about 10.

n) $C_1$–$C_{22}$ linear $C_3$–$C_{22}$ branched thioalkyl, $C_1$–$C_{22}$ linear, $C_3$–$C_{22}$ branched substituted thioalkyl, and mixtures thereof;

o) ester units of the formula —$CO_2R^9$ wherein $R^9$ is $C_1$–$C_{22}$ alkyl, $C_3$–$C_{22}$ branched alkyl, $C_2$–$C_{22}$ alkenyl, $C_3$–$C_{22}$ branched alkenyl, all of which can be substituted with halogen; poly-hydroxyl substituted $C_3$–$C_{22}$ alkyl, $C_3$–$C_{22}$ glycol; $C_1$–$C_{22}$ alkoxy, $C_3$–$C_{22}$ branched alkoxy; substituted and unsubstituted aryl, alkylenearyl, aryloxy, oxyalkylenearyl, alkyleneoxyaryl; preferably $C_1$–$C_{22}$ alkyl, $C_3$–$C_{22}$ branched alkyl, and mixtures thereof;

p) alkyleneamino units having the formula:

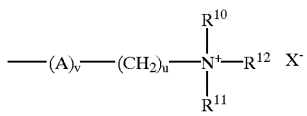

wherein $R^{10}$, and $R^{11}$ are each a $C_1$–$C_{22}$ alkyl, $C_3$–$C_{22}$ branched alkyl, $C_2$–$C_{22}$ alkenyl, $C_3$–$C_{22}$ branched alkenyl, $R^{12}$ is hydrogen, $C_1$–$C_{22}$ alkyl, $C_3$–$C_{22}$ branched alkyl, $C_2$–$C_{22}$ alkenyl, $C_3$–$C_{22}$ branched alkenyl and mixtures thereof, the index v is 0 or 1; X is a other water soluble anion, u is from 0 to 22, preferably u is from 3 to about 10. Examples of water soluble anions include organic species such as fumarate, tartrate, oxalate and the like, inorganic species include chloride, bromide, sulfate, hydrogen sulfate, phosphate and the like;

q) an amino unit of the formula

—$NR^{17}R^{18}$ wherein $R^{17}$ and $R^{18}$ are each a $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

r) alkylethyleneoxy units having the formula:

—$(A)_v$—$(CH_2)_y(OCH_2CH_2)_xZ$ wherein Z is hydrogen, hydroxyl, —$CO_2H$, —$SO_3^-M^+$, —$OSO_3^-M^+$, $C_1$–$C_6$ alkoxy, substituted and unsubstituted aryl, substituted and unsubstituted aryloxy; alkyleneamino as defined herein above; or mixtures thereof; A units comprise nitrogen or oxygen, preferably oxygen; M is a water soluble cation; v is 0 or 1; x is from 0 to 100, preferably from 0 to 20, more preferably from 0 to 5; y is from 0 to 12, preferably from 1 to 4; however, no peroxide —O—O— bonds are contained within the photobleaching compounds of the present invention;

s) siloxy and substituted siloxy of the formula —$OSiR^{19}R^{20}R^{21}$ wherein each $R^{19}$, $R^{20}$, and $R^{21}$ is independently selected from the group consisting of $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof, substituted or unsubstituted aryl, aryloxy; alkylethyleneoxy units of the formula:

—$(A)_v$—$(CH_2)_y(OCH_2CH_2)_xZ$ wherein Z is hydrogen, hydroxyl, $C_1$–$C_{30}$ alkyl, —$CO_2H$, —$SO_3^-M^+$, —$OSO_3^-M^+$, $C_1$–$C_6$ alkoxy; substituted or unsubstituted aryl, and aryloxy; alkyleneamino as defined herein above, and mixtures thereof, preferably hydrogen or $C_1$–$C_6$ alkyl, more preferably methyl; v is 0 or 1; x is from 1 to 100, preferably from 0 to about 20, more preferably from 3 to about 10; and y is from 0 to 12, preferably from about 0 to about 5.

Harvester Units, D

The photochemical singlet oxygen generators of the present invention comprise one or more "harvester units". For the purposes of the present invention "harvester units" are defined as "units which increase the efficiency of singlet oxygen production by collecting un-usable energy in the form of ultra violet radiation then transfering said absorbed energy to the photosensitizer unit of the singlet oxygen generator". Typically, D units have the formula

—$L^1$—E or

—$L^1$—B—$[L^2$—$E]_m$ or

—$L^1$R wherein E is an aromatic unit and R is the same as defined herein above. The requirements for an E unit according to the present invention are:

a) absorbs ultra violet radiation at a wavelength of from about 200 nm to about 400 nm;

b) has an extinction coefficient of at least about 100; and c) has a fluorescence spectrum which overlaps an absorption band of said photosensitizer unit By way of illustration and without limitation, examples of E units are naphthalene, anthracene, p-terphenyl, and mixture thereof Harvester D units also comprise $L^1$ and $L^2$ linking units, wherein the $L^1$ and $L^2$ units when taken together with a B unit comprise a total of at least 20 continuous covalent bonds from said P unit to said E units; m is from 2 to 4.

Preferred $L^1$ and $L^2$ units are independently selected from the group consisting of oxygen, linear or branched alkylene, linear or branched alkenylene; linear or branched alkyleneoxy, substituted or unsubstituted arylene, substituted or unsubstituted alkylenearylene, substituted or unsubstituted aryleneoxy, substituted or unsubstituted oxyalkylenearylene, substituted or unsubstituted alkyleneoxyarylene, and mixtures thereof, defined herein further below.

For the purposes of the present invention an oxygen molecule may serve as a suitable $L^1$ unit, preferably when directly bonded to a branching unit to form a moiety having the general formula:

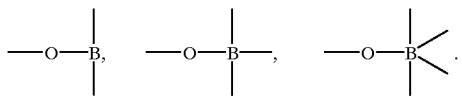

For the purposes of the present invention linear or branched alkylene moieties are defined as units having the formula:

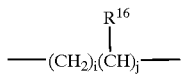

wherein $R^{16}$ is $C_1$–$C_4$ alkyl; the index i has the value from 1 to 30, the index j has the value from 1 to 30. If only one linking group $L^1$ is present between the photosensitizer unit P and the harvester unit E then the value of i+j must be at least 20.

For the purposes of the present invention linear or branched alkenylene moieties are defined as moieties comprising one or more units, or combinations of units having the formula:

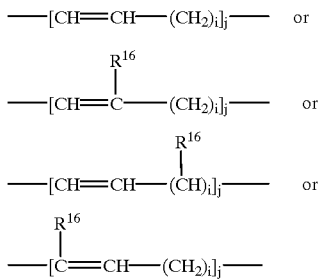

wherein $R^{16}$ is $C_1$–$C_4$ alkyl; the index i has the value from 1 to 30. In the case where only one linking group $L^1$ is present between the photosensitizer unit P and the harvester unit E then the values of i and j must be sufficient to provide at least 20 covalent bonds between said photosensitizer unit P and said harvester unit E.

For the purposes of the present invention linear or branched alkyleneoxy moieties which comprise the $L^1$ or $L^2$ units described herein below, are defined as units or a combination of units having the formula:

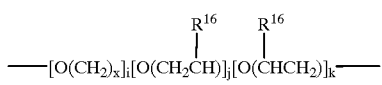

wherein $R^{16}$ is $C_1$–$C_4$ alkyl; the index x has the value from 2 to 4; whereas the values of the indices i, j and k must have sufficient value for at least 20 covalent bonds between the photosensitizer unit P and the harvester unit E.

For the purposes of the present invention substituted or unsubstituted arylene moieties are defined as 1,2-phenylene, 1,3-phenylene, and 1,4-phenylene units having the formula:

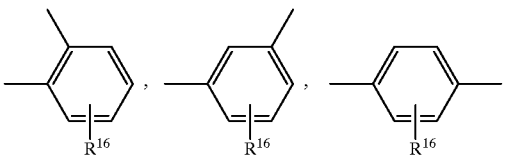

wherein $R^{16}$ is hydrogen, $C_1$–$C_4$ alkyl, and mixtures thereof. Arylene units may be used alone or in combination with other suitable moieties to form $L^1$ and $L^2$ units.

For the purposes of the present invention substituted or unsubstituted alkylenearylene moieties are defined as 1,2-phenylene, 1,3-phenylene, and 1,4-phenylene units having the formula:

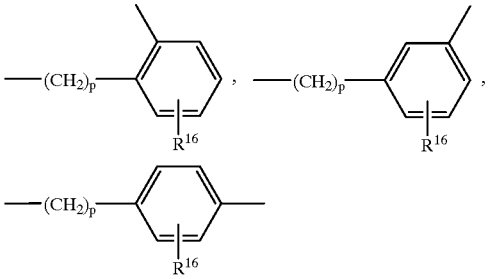

wherein $R^{16}$ is hydrogen, $C_1$–$C_4$ alkyl, and mixtures thereof alkylenearylene units may be used alone or in combination with other suitable moieties to form $L^1$ and $L^2$ units.

For the purposes of the present invention substituted and unsubstituted aryleneoxy moieties are defined as 1,2-phenyleneoxy, 1,3-phenyleneoxy, and 1,4-phenyleneoxy units having the formula:

wherein $R^{16}$ is hydrogen, $C_1$–$C_4$ alkyl, and mixtures thereof. Aryleneoxy units may be used alone or in combination with other suitable moieties to form $L^1$ and $L^2$ units.

For the purposes of the present invention substituted and unsubstituted oxyalkylenearylene moieties are defined as 1,2-oxyalkylenephenylene, 1,3-oxyalkylenephenylene, and 1,4-oxyalkylenephenylene units having the formula:

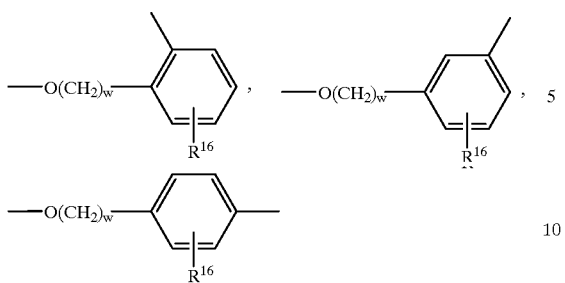

wherein $R^{16}$ is hydrogen, $C_1$–$C_4$ alkyl, and mixtures thereof, the index w has the value from 1 to 30. Oxyalkylenarylene units may be used alone or in combination with other suitable moieties to form $L^1$ and $L^2$ units.

For the purposes of the present invention substituted and unsubstituted alkyleneoxyarylene moieties are defined as 1,2-alkyleneoxyphenylene, 1,3-alkyleneoxyphenylene, and 1,4-alkyleneoxyphenylene units having the formula:

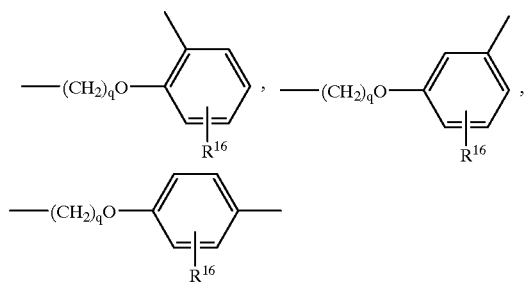

wherein $R^{16}$ is hydrogen, $C_1$–$C_4$ alkyl, and mixtures thereof, the index q has the value from 1 to 30. Alkyleneoxyarylene units may be used alone or in combination with other suitable moieties to form $L^1$ and $L^2$ units.

The D units of the present invention also optionally comprise branching units B said units having the formula:

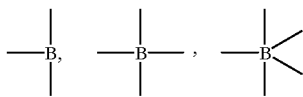

wherein B is selected from the group consisting of boron, aluminum, nitrogen, phosphorous, carbon, silicon, tin, germanium, and mixtures thereof, preferably carbon or silicon, more preferably carbon.

Without wishing to be limited by theory, the "harvester groups" according to the present invention act to convert light energy of a wavelength outside the absorption spectrum of the photosensitizer into energy which is transferred to the photosensitizing unit via a "Foster Energy Transfer" which is a direct energy transfer process. Therefore by this process the harvester units increase the photo efficiency of the photosensitizing unit by first absorbing electromagnetic radiation in the ultra violet spectral region then transfering this energy to the photosensitizer unit. This process acts to "widen" or "expand" the absorption spectra of the photosensitizer unit. In order to accomplish this energy transfer the harvester groups of the present invention must have their fluorescence emission bands at wavelengths in which the photosensitizer unit absorbs light. Therefore some or all of the fluorescence emission spectrum of the E units must overlap the absorption spectrum of the photosensitizer P units.

The aromatic moieties which comprise the E units of the present invention have extinction coefficients that are at least 100, preferably at least 1000, more preferably at least 10,000.

Substantivity and Solubility Mediating Axial R units

The singlet oxygen generators of the present invention optionally comprise an R unit. Substantivity and solubility mediating axial R units, are bonded directly to the photoactive metal or non-metal atom which is chelated by the photosensitizing unit and occupies a position axial to the essentially planar photosensitizing unit. The utility of each R unit is primarily directed to the solubility or substantivity properties of the compounds of the present invention. The selection of an R unit can be made, in addition to, or in lieu of, solubility requirements, and be totally directed instead to the "substantivity" or "non-substantivity" of the compound. R units are nonionic, cationic, or anionic units.

For the purposes of the present invention the term "substantivity" is defined as "the ability for a molecule to bind, adhere, or have a general affinity for a surface" inter alia fabric and hard surfaces.

The axial R units suitable for use as substantivity or solubility mediation units of the present invention include:

a) hydrogen;
b) halogen;
c) hydroxyl;
d) $C_1$–$C_{22}$ alkyl, $C_3$–$C_{22}$ branched alkyl, $C_2$–$C_{22}$ alkenyl, $C_3$–$C_{22}$ branched alkenyl;
e) halogen substituted $C_1$–$C_{22}$ alkyl, $C_3$–$C_{22}$ branched allyl, $C_2$–$C_{22}$ alkenyl, $C_3$–$C_{22}$ branched alkenyl;
f) polyhydroxyl substituted $C_3$–$C_{22}$ allyl;
g) $C_1$–$C_{22}$ alkoxy, preferably $C_1$–$C_4$ alkoxy, more preferred methoxy;
h) branched alkoxy having the formula

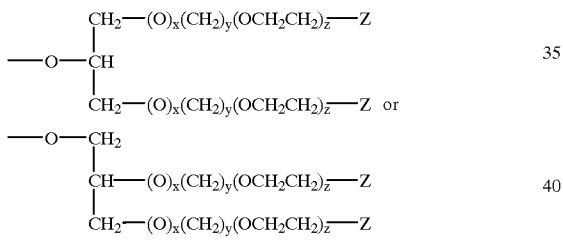

wherein Z is hydrogen, hydroxyl, $C_1$–$C_{30}$ linear alkyl, $C_1$–$C_{30}$ branched alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, and mixtures thereof; M is a water soluble cation in sufficient amount to satisfy charge balance; x is 0 or 1, each y independently has the value from 0 to 6, preferably from 0 to 6; each z independently has the value from 0 to 100, preferably from 0 to about 0, more preferably from 0 to about 3;

i) substituted aryl, and unsubstituted aryl having the formula:

wherein $R^{13}$ and $R^{14}$ are independently selected from the group consisting of hydrogen, $C_1$–$C_6$ alkyl, $C_3$–$C_6$ alkenyl, $C_1$–$C_6$ alkoxy, $C_1$–$C_6$ branched alkoxy, halogen, —$CO_2^-M^+$, —$SO_3^-M^+$, —$OSO_3^-M^+$, —$N(R^{15})_2$, and —$N^+(R^{15})_3X^-$ wherein each $R^{15}$ is independently hydrogen or $C_1$–$C_4$ alkyl; and mixtures thereof; preferably hydrogen $C_1$–$C_6$ alkyl, —$CO_2^-M^+$, —$OSO_3^-M^+$, —$OSO_3^-M^+$, and mixtures thereof, more preferably $R^{13}$ or $R^{14}$ is hydrogen and the other moiety is $C_1$–$C_6$ alkyl; wherein M is a water soluble cation and X is a water soluble anion.

j) substituted alkylenearyl and unsubstituted alkylenearyl having the formula:

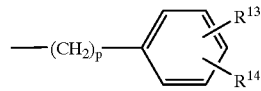

wherein $R^{13}$ and $R^{14}$ are as defined above, p is from 1 to about 10.

k) substituted aryloxy and unsubstituted aryloxy having the formula:

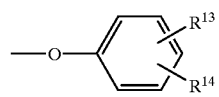

wherein $R^{13}$ and $R^{14}$ are as defined above.

l) substituted alkyleneoxyaryl and unsubstituted alkyleneoxyaryl units are defined as moieties having the formula:

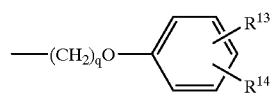

wherein $R^{13}$ and $R^{14}$ are as defined above, q is from 0 to about 10.

m) substituted oxyalkylenearyl and unsubstituted oxyalkylenearyl having the formula:

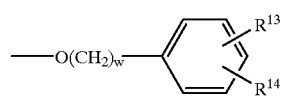

wherein $R^{13}$ and $R^{14}$ are as defined above, w is from about 1 to about 10.

n) $C_1$–$C_{22}$ linear, $C_3$–$C_{22}$ branched thioalkyl, $C_1$–$C_{22}$ linear, $C_3$–$C_{22}$ branched substituted thioalkyl and mixtures thereof;

o) carboxylate units of the formula

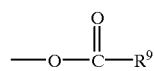

wherein $R^9$ is $C_1$–$C_{22}$ alkyl, $C_3$–$C_{22}$ branched alkyl, $C_2$–$C_{22}$ alkenyl, $C_3$–$C_{22}$ branched alkenyl, all of which can be substituted with halogen; poly-hydroxyl substituted $C_3$–$C_{22}$ alkyl, $C_3$–$C_{22}$ glycol; $C_1$–$C_{22}$ alkoxy, $C_3$–$C_{22}$ branched alkoxy; substituted and unsubstituted aryl, alkylenearyl, aryloxy, oxyalkylenearyl, alkyleneoxyaryl; preferably $C_1$–$C_{22}$ alkyl, $C_3$–$C_{22}$ branched alkyl, and mixtures thereof;

p) alkyleneamino units having the formula:

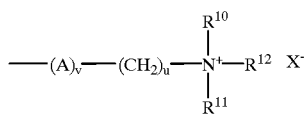

wherein $R^{10}$, and $R^{11}$ are each a $C_1$–$C_{22}$ alkyl, $C_3$–$C_{22}$ branched alkyl, $C_2$–$C_{22}$ alkenyl, $C_3$–$C_{22}$ branched alkenyl, $R^{12}$ is hydrogen, $C_1$–$C_{22}$ alkyl, $C_3$–$C_{22}$ branched alkyl, $C_2$–$C_{22}$ alkenyl, $C_3$–$C_{22}$ branched alkenyl and mixtures thereof, the index v is 0 or 1; X is a other water soluble anion, u is from 0 to 22, preferably u is from 3 to about 10. Examples of water soluble anions include organic species such as fumarate, tartrate, oxalate and the like, inorganic species include chloride, bromide, sulfate, hydrogen sulfate, phosphate and the like;

q) an amino unit of the formula

wherein $R^{17}$ and $R^{18}$ are each a $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

r) alkylethyleneoxy units having the formula:

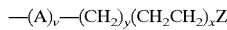

wherein Z is hydrogen, hydroxyl, —$CO_2H$, —$SO_3^-M^+$, —$OSO_3^-M^+$, $C_1$–$C_6$ alkoxy, substituted and unsubstituted aryl, substituted and unsubstituted aryloxy; alkyleneamino as defined herein above; or mixtures thereof; A units comprise nitrogen or oxygen, preferably oxygen; M is a water soluble cation; v is 0 or 1; x is from 0 to 100, preferably from 0 to 20, more preferably from 0 to 5; y is from 0 to 12, preferably from 1 to 4; however, no peroxide —O—O— bonds are contained within the photobleaching compounds of the present invention;

s) siloxy and substituted siloxy of the formula —$OSiR^{19}R^{20}R^{21}$ wherein each $R^{19}$, $R^{20}$, and $R^{21}$ is independently selected from the group consisting of $C_1$–$C_{22}$ alkyl, $C_3$–$C_{22}$ branched alkyl, $C_2C_{22}$ alkenyl, $C_3$–$C_{22}$ branched alkenyl, or mixtures thereof, substituted or unsubstituted aryl, aryloxy; alkylethyleneoxy units of the formula:

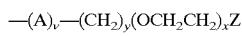

wherein Z is hydrogen, hydroxyl, $C_1$–$C_{30}$ alkyl, —$CO_2H$, —$SO_3^-M^+$, —$OSO_3^-M^+$, $C_1$–$C_6$ alkoxy; substituted or unsubstituted aryl, and aryloxy; alkyleneamino as defined herein above, and mixtures thereof, preferably hydrogen or $C_1$–$C_6$ alkyl, more preferably methyl; v is 0 or 1; x is from 1 to 100, preferably from 0 to about 20, more preferably from 3 to about 10; and y is from 0 to 12, preferably from about 0 to about 5.

According to the present invention the preferred axial R units comprise moieties having the formula

and

wherein Y is a linking moiety selected from the group consisting of O, $CR^{25}R^{26}$, $OSiR^{25}R^{26}$, $OSnR^{25}R^{26}$, and mixtures thereof; wherein $R^{25}$ and $R^{26}$ are hydrogen, $C_1$–$C_4$ alkyl, halogen, and mixtures thereof; i is 0 or 1, j is from 1 to 3;

K is a ligand selected from the group consisting of:

a) $C_1$–$C_{30}$ linear alkyl, $C_3$–$C_{30}$ branched alkyl, $C_2$–$C_{30}$ linear alkenyl, $C_3$–$C_{30}$ branched alkenyl, $C_6$–$C_{20}$ aryl, $C_7$–$C_{20}$ arylalkyl, $C_7$–$C_{20}$ alkylaryl, and mixtures thereof;

b) an alkylethyleneoxy unit of the formula

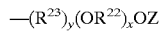

wherein Z is selected from the group consisting of hydrogen, $C_1$–$C_{20}$ alkyl, $C_3$–$C_{20}$ branched alkyl, $C_2$–$C_{20}$ linear alkenyl, $C_3$–$C_{20}$ branched alkenyl, $C_6$–$C_{20}$ aryl, $C_7$–$C_{30}$ arylalkyl, $C_6$–$C_{20}$ alkylaryl, and mixtures thereof; $R^{22}$ is selected from the group consisting of $C_1$–$C_4$ linear alkylene, $C_3$–$C_4$ branched alkylene, $C_3$–$C_6$ hydroxyalkylene, and mixtures thereof; $R^{23}$ is selected from the group consisting of $C_2$–$C_{20}$ alkylene, $C_3$–$C_{20}$ branched alkylene, $C_6$–$C_{20}$ arylene, $C_7$–$C_{30}$ arylalkylene, $C_7$–$C_{30}$ alkylarylene, and mixtures thereof; x is from 1 to 100; y is 0 or 1; and Q is an ionic moiety having the formula:

wherein $R^{24}$ is selected from the group consisting of $C_3$–$C_{30}$ linear alkylene, $C_3$–$C_{30}$ branched alkylene, $C_2$–$C_{30}$ linear alkenylene, $C_3$–$C_{30}$ branched alkenylene, $C_6$–$C_{16}$ arylene, and mixtures thereof; W is selected from the group consisting of —$CO_2^-M^+$, —$SO_3^-M^+$, $OSO_3^-M^+$; $PO_3^{2-}M^+$, —$OPO_3^-M^+$, —$N^+(R^{27})_3X^-$; wherein $R^{27}$ is independently hydrogen, $C_1$–$C_6$ alkyl, —$(CH_2)_nOH$, —$(CH_2CH_2O)_nH$, and mixtures thereof; wherein n is from 1 to 4; M is a water soluble cation of sufficient charge to provide electronic neutrality and X is a water soluble anion as defined herein above.

Preferred axial R units are alkyl alkyleneoxy units of the formula

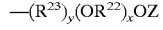

wherein Z is selected from the group consisting of hydrogen, $C_7$–$C_{20}$ linear alkyl, $C_3$–$C_{20}$ branched allyl, $C_2$–$C_{20}$ linear alkenyl, $C_3$–$C_{20}$ branched alkenyl, $C_6$–$C_{10}$ aryl, $C_7$–$C_{20}$ arylalkyl, $C_7$–$C_{20}$ alkylaryl, and mixtures thereof; $R^{22}$ is selected from the group consisting of $C_1$–$C_4$ linear alkylene, $C_3$–$C_4$ branched alkylene, and mixtures thereof; $R^{23}$ is selected from the group consisting of $C_2$–$C_6$ alkylene, $C_3$–$C_6$ branched alkylene, $C_6$–$C_{10}$ arylene, and mixtures thereof; x is from 1 to 50; y is 0 or 1.

More preferred axial R units comprise y equal to 0, Z is hydrogen, $C_1$–$C_{20}$ alkyl, $C_3$–$C_{20}$ branched alkyl, $C_6$–$C_{10}$ aryl, and mixtures thereof, most preferred Z is hydrogen or $C_6$–$C_{20}$ linear alkyl, $C_{10}$–$C_{20}$ branched alkyl; $R^{22}$ is $C_1$–$C_4$ linear or $C_3$–$C_4$ branched alkylene.

Also preferred R units having the formula:

wherein Y is a linking moiety selected from the group consisting of O, $CR^{25}R^{26}$ $OSiR^{25}R^{26}$, $OSnR^{25}R^{26}$, and mixtures thereof; i is 0 or 1, j is from 1 to 3; Q is an ionic moiety having the formula:

$$-R^{24}-W$$

wherein $R^{24}$ is selected from the group consisting of $C_2$–$C_{20}$ linear alkylene, $C_3$–$C_{20}$ branched alkylene, $C_2$–$C_{20}$ linear alkenylene, $C_3$–$C_{20}$ branched alkenylene, $C_6$–$C_{10}$ arylene, and mixtures thereof; W is selected from the group consisting of —$CO_2^-M^+$, —$SO_3^-M^+$, —$OSO_3^-M^+$; $PO_3^{2-}M^+$, —$OPO_3^-M^+$, —$N^+(R^{27})_3X^-$; wherein $R^{27}$ is independently hydrogen, $C_1$–$C_6$ alkyl, —$(CH_2)_nH$, —$(CH_2CH_2O)_nH$, and mixtures thereof; wherein n is from 1 to 4; M is a water soluble cation of sufficient charge to provide electronic neutrality and X is a water soluble anion as defined herein above.

A preferred hydrophilic R has the index i equal to 1; $R^{24}$ is $C_3$–$C_{20}$ linear alkylene, $C_3$–$C_{20}$ branched alkylene; W is —$CO_2^-M^+$, —$SO_3^-M^+$, —$OSO_3^-M^+$; M is a water soluble cation of sufficient charge to provide electronic neutrality.

Examples of Y units suitable for use in R units having the formula:

$$-Y_i-K_j$$

have the formula

—O—$K^1$,

—Sn—$K^1$,

—OSn—$K^1$ wherein i is equal to 1 and j is equal to 1. Further examples have the formula

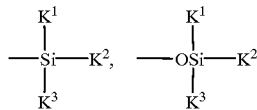

wherein i is equal to 1 and j is equal to 3. The above examples also apply to Y units when used with Q ionic moieties.

An example of a preferred photochemical singlet oxygen generator according to the present invention has the following formula:

wherein the photosensitizer unit P comprises an unsubstituted silicon(IV) phthalocyanine ($R^1$–$R^4$ of each benzene ring is hydrogen) and there are two identical D "harvester" units wherein $L^1$ is an alkyleneoxy unit having the formula:

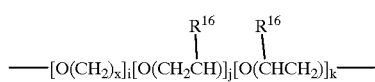

wherein the indices j and k are equal to 0, x is equal to 2, and i is equal to 15, and the E unit is a-naphthyl. The number of covalent bonds between the photosensitizer unit P and the aromatic harvester unit is greater than 20.

Further examples of photochemical singlet oxygen generators according to the present invention are the silicon(IV) phthalocyanines having the general formula:

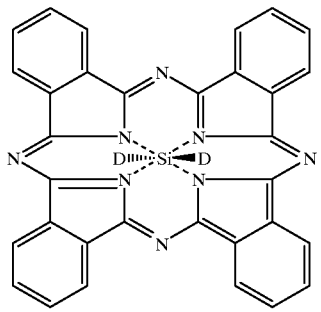

wherein for the first example each D unit has the formula:

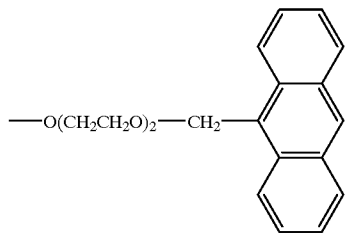

wherein $L^1$ is and alkyleneoxy wherein j and k are equal to 0, x is equal to 2 and i is equal to 2, E is a methyleneanthracene moiety.

A further example comprises two D units having the formula:

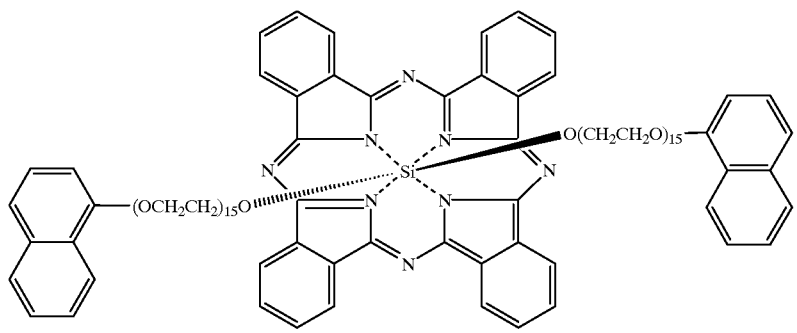

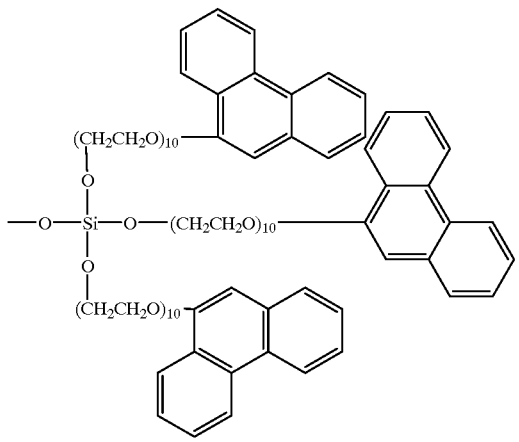

wherein $L^1$ is oxygen, B is silicon, each $L^2$ is an alkyleneoxy unit wherein j and k are both equal to 0, x is equal to 2 and i is equal to 10, each E unit is a phenanthrene moiety.

The present invention also relates to laundry detergent compositions comprising:

a) at least about 0.1%, preferably from about 0.1% to about 30%/0, more preferably from about 1% to about 30%, most preferably from about 5% to about 20% by weight, of a detersive surfactant, said detersive surfactant selected from the group consisting of anionic, cationic, zwitterionic, nonionic, and ampholytic surfactants, and mixtures thereof;

b) at least about 0.001 ppm, preferably from about 0.01 to about 10000 ppm, more preferably from about 0.1 to about 5000 ppm, most preferably form about 10 to about 1000 ppm, of a source of singlet oxygen having the formula

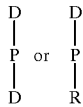

wherein P is a photosensitizing group; each D is independently a moiety which is capable of enhancing the production of singlet oxygen; and R is an axial moiety which mediates the solubility or substantivity of the singlet oxygen generator as described herein above; and c) the balance carriers and adjunct ingredients.

It is also an object of the present invention to provide hard surface cleaning compositions which can be used to clean or disinfect hard surfaces, said compositions comprising:

a) at least about 0.1%, preferably from about 0.1% to about $^{30}$%, more preferably from about 1% to about 30%, most preferably from about 5% to about 20% by weight, of a detersive surfactant;

b) at least about 0.001 ppm, preferably from about 0.01 to about 10000 ppm, more preferably from about 0.1 to about 5000 ppm, most preferably form about 10 to about 1000 ppm, of a source of singlet oxygen having the formula

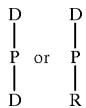

wherein P is a photosensitizing group; each D is independently a moiety which is capable of enhancing the production of singlet oxygen; and R is an axial moiety which mediates the solubility or substantivity of the singlet oxygen generator as described herein above; and c) the balance carriers and adjunct ingredients.

The laundry detergent compositions of the present invention may be liquid, granular or semi-solid, for example a gel, paste, or viscous cream.

The present invention also relates to a method for cleaning a stained fabric comprising contacting a stained fabric in need of cleaning with an aqueous cleaning solution comprising at least 0.001% of the singlet oxygen generator according to the present invention followed by exposing the surface of the treated fabric to a source of light having a minimal wavelength range from about 300 to about 1200 nanometers.

The present invention also relates to a method for cleaning a hard surface comprising contacting a hard surface in need of cleaning with an aqueous cleaning composition comprising at least 0.001 % of the singlet oxygen generator according to the present invention and exposing the hard surface to a source of light having a minimal wavelength range from about 300 to about 1200 nanometers.

Surfactant

The instant singlet oxygen generator containing compositions comprise from about 0.001% to about 60% by weight of a surfactant selected from the group consisting of anionic, nonionic; ampholytic and zwitterinonic surface active agents. For liquid systems, surfactant is preferably present to the extent of from about 0.1% to 20% by weight of the composition. For solid (i.e. granular) and viscous semi-solid (i.e. gelatinous, pastes, etc.) systems, surfactant is preferably present to the extent of from about 1.5% to 30% by weight of the composition.

Nonlimiting examples of surfactants useful herein typically at levels from about 1% to about 55%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)$ $CH_3$ and $CH_3 (CH_2)_y(CHOSO_3^-M^+)$ $CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10}$–$C_{18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and ampholteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N—(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are described further herein and are listed in standard texts.

Anionic surfactants can be broadly described as the water-soluble salts, particularly the alkali metal salts, of organic sulfuric reaction products having in their molecular structure an alkyl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic synthetic detergents which can form the surfactant component of the compositions of the present invention are the sodium or potassium alkyl sulfates, especially those obtained by sulfating the higher alcohols (C8–18 carbon atoms) produced by reducing the glycerides of tallow or coconut oil; sodium or potassium alkyl benzene sulfonates, in which the alkyl group contains from about 9 to about 15 carbon atoms, (the alkyl radical can be a straight or branched aliphatic chain); sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid ester of the reaction product of one mole of a higher fatty alcohol (e.g. tallow or coconut alcohols) and about 1 to about 10 moles of ethylene oxide; sodium or potassium salts of alkyl phenol ethylene oxide ether sulfates with about 1 to about 10 units of ethylene oxide per molecule and in which the alkyl radicals contain from 8 to 12 carbon atoms; the reaction products of fatty acids are derived from coconut oil sodium or potassium salts of tatty acid amides of a methyl tauride in which the fatty acids, for example, are derived from coconut oil and sodium or potassium beta-acetoxy- or beta-acetamido-alkanesulfonates where the alkane has from 8 to 22 carbon atoms.

Additionally, secondary alkyl sulfates may be used by the formulator exclusively or in conjunction with other surfactant materials and the following identifies and illustrates the differences between sulfated surfactants and otherwise conventional alkyl sulfate surfactants. Non-limiting examples of such ingredients are as follows.

Conventional primary alkyl sulfates, such as those illustrated above, have the general formula ROSO3—M+ wherein R is typically a linear C8–22 hydrocarbyl group and M is a water solublizing cation. Branched chain primary alkyl sulfate surfactants (i.e., branched-chain "PAS") having 8–20 carbon atoms are also know; see, for example, Eur. Pat. Appl. 439,316, Smith et al., filed Jan. 21, 1991.

Conventional secondary alkyl sulfate surfactants are those materials which have the sulfate moiety distributed randomly along the hydrocarbyl "backbone" of the molecule. Such materials may be depicted by the structure

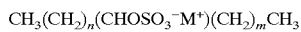

wherein m and n are integers of 2 of greater and the sum of m+n is typically about 9 to 17, and M is a water-solublizing cation.

The aforementioned secondary alkyl sulfates are those prepared by the addition of $H_2SO_4$ to olefins. A typical synthesis using alpha olefins and sulfuric acid is disclosed in U.S. Pat. No. 3,234,258, Morris, issued Feb. 8, 1966 or in U.S. Pat. No. 5,075,041, Lutz, issued Dec. 24, 1991. The synthesis conducted in solvents which afford the secondary (2,3) alkyl sulfates on cooling, yields products which, when purified to remove the unreacted materials, randomly sulfated materials, unsulfated by-products such as C10 and higher alcohols, secondary olefin sulfonates, and the like, are typically 90+% pure mixture of 2- and 3-sulfated materials (some sodium sulfate may be present) and are white, non tacky, apparently crystalline, solids. Some 2,3-disulfates may also be present, but generally comprise no more than 5% of the mixture of secondary (2,3) alkyl mono-sulfates. Such materials are available as under the name "DAN", e.g., "DAN 200" from Shell Oil Company.

Adjunct Materials

The following are non-limiting examples of adjunct ingredients suitable for use in either laundry or hard surface cleaning or disinfecting compositions according to the present invention.

Chelating Agents

The photo disinfectant compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that certain chelating agents will interact with photodisinfectants of the present invention to increase their absorbency in the visible light spectrum. This is a process that is due to the ability of chelating agents to help effect the "substantiveness" of the compounds of the present invention.

Amino carboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts therein and mixtures therein.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

If utilized, these chelating agents will generally comprise from about 0.1% to about 10% by weight of the detergent compositions herein. More preferably, if utilized, the chelating agents will comprise from about 0.1% to about 3.0% by weight of such compositions.

Inert Salts

The inert salts (filler salts) used in the compositions of the present invention can be any water-soluble inorganic or organic salt or mixtures of such salts which do not destabilize any surfactant present. For the purposed of the present invention, "water-soluble" means having a solubility in water of at least I gram per 100 grams of water at 20° C. Examples of suitable salts include various alkali metal and/or alkali earth metal sulfate, chlorides, borates, bromides, fluorides, phosphates, carbonates, bicarbonates, citrates, acetates, lactates, etc.

Specific examples of suitable salts include sodium sulfate, sodium chloride, potassium chloride, sodium carbonate, potassium sulfate, lithium chloride, lithium sulfate, tripotassium phosphate, sodium borate, potassium bromide, potassium fluoride, sodium bicarbonate, magnesium sulfate, magnesium chloride, sodium citrate, sodium acetate, magnesium lactate, sodium fluoride. The preferred salts are inorganic salts preferably the alkali metal sulfates and chlorides. Particularly preferred salts, because of their low cost are sodium sulfate and sodium chloride. The salts are present in the compositions at levels of from 0% to 40%. preferably 10% to 20%.

EXAMPLE 1

Preparation of silicon phthalocyanine dichloride

To a mixture of 1,3diiminoisoindoline (0.333 gm, 2.3 mmole) and anhydrous quinoline (15 mL) under argon blanketing is added silicon tetrachloride (1.1 g, 6.5 mmole). The mixture is lowered into an oil bath at 60° C. for 0.5 hr, heated to reflux over 0.5 hr, stirred at reflux for an additional 0.5 hr and cooled over 1 hr. To this solution is added methanol (10 mL) and the resultant mixture is allowed to stand at room temperature for 24 hr. The blue solid which forms upon standing is filtered off, rinsed twice with 10 mL portions of methanol, dried under vacuum at 120° C. and used without further purification.

The above procedure is suitable for use in preparing silicon naphthalocyanine dichloride using 1,3-diiminobenz-[f]-isoindoline.

EXAMPLE 2

Preparation of 1:3 silicon(VI)phthalo/ naphthalocyanine dichloride

To a mixture of 1,3-diiminoisoindoline (0.333 gm, 2.3 mmole), 1,3-diiminobenz[f]-isoindoline (1.35 gm, 6.9 mmole) and anhydrous quinoline (15 mL) under argon blanketing is added silicon tetrachloride (2.21 g, 12.9 mmole). The mixture is lowered into an oil bath at 60° C. for 0.5 hr, heated to reflux over 0.5 hr, stirred at reflux 0.5 hr and cooled over 1 hr. To this solution is added methanol (10 mL) and the resultant mixture is allowed stand at room temperature for 24 hr. The green solid which forms is removed by filtration, rinsed twice with 10 mL portions of methanol, dried under vacuum at 120° C. and used without further purification.

EXAMPLE 3

Preparation of silicon phthalocyanine dihydroxide

Silicon (IV) phthalocyanine dichloride (2 gm, 3.3 mmole) is added to a refluxing solution of sodium methoxide (0.8 g, 14.8 mmole) in 95% wet ethanol (15 mL). The reaction mixture is refluxed 4 hr then cooled to room temperature. The resulting product is collected by filtration, rinsed with water and used without subsequent purification.

The above procedure is suitable for use in preparing silicon naphthalocyanine dihydroxide, and 1:3 silicon (IV) phthalo/naphthalocyanine dihydroxide.

EXAMPLE 4

Preparation of dilithium naphthalocyanine

To a refluxing solution of 2,3-dicyanonaphthalene (10 gm, 56.1 mmole) in anhydrous 1-butanol (300 mL) is added lithium shot (1.56 gm, 224.5 mmole). The solution is refluxed 6 hr under a blanket of argon after which time the solution is cooled, diluted with absolute methanol (500 mL) and allowed to stand at 0° C. for 18 hr. The green solid which results is collected by filtration, dried under vacuum at 80° C. and used without further purification.

The above procedure is suitable for use in preparing 1,4,8,11,15,18,22,25-octabutoxy-29,31-dilithium phthalocyanine from 3,6-dibutoxyphthalonitrile; 2,3,9,10,16,17,23,24-octachloro29-31-dilithium phthalocyanine from 4,5-dichlorophthalonitrile; and tetrabutoxy-29,31-dilithium phthalocyanine from 3-butoxyphthalonitrile wherein there is a mixture of isomers.

EXAMPLE 5

Preparation of naphthalocyanine

To a solution of dilithium naphthalocyanine (2 gm, 2.75 mmole) in N,N-Dimethylformamide (200 mL) is added 1N hydrochloric acid (10 mL). The solution is stirred at room temperature for 1 hr. To this solution is added distilled water (200 mL) over approximately 0.5 hr. The green solid which forms is collected by filtration, dried under vacuum at 100° C. and used without further purification.

The above procedure is suitable for use in preparing 1,4,8,11,15,18,22,25-octabutoxy-29H,31H-phthalocyanine; 2,3,9,10,16,17,23,24-octachloro-29H,31H-phthalocyanine; and tetrabutoxy-29H,31H-phthalocyanine.

EXAMPLE 6

Ethoxylation of 1-naphthaleneethanol to an average of 15 ethyleneoxy units.

To a dried 250 mL 3 neck round bottom flask, fitted with a gas inlet tube, overhead mechanical stirrer, and a Y-tube which is equipped with a thermometer and a gas outlet tube is charged 1-naphthaleneethanol (20 gm, 116.3 mmole). Under nitrogen blanketing sodium metal (0.11 gm, 5 mmole) is added and the resulting mixture heated to from about 120 to about 140° C. With vigorous stirring, ethylene oxide gas (80 gm, 1.82 a mole) is added while maintaining the within the range of from 120 to about 140° C. After addition of ethylene oxide is complete, nitrogen is swept through the apparatus for 20–30 minutes as the reaction solution is allowed to cool. The yellow/brown liquid product which results is used without further purification.

The above procedure is suitable for use to ethoxylate 1-anthracene to an average degree of ethoxylation of 15 (E15).

EXAMPLE 7

Preparation of silicon phthalocyanine-di-[pentadecyl (ethylene glycol) mono-1-ethylnaphthalene ether]

Silicon phthalocyanine dihydroxide (0.25 gm, 0.44 mmole), anhydrous 1-naphthalenepentadecylethylene glycol (10 gm, 17.4 mmole) and xylenes (175 mL) are combined and heated to reflux over 1.5 hr. The solution is continued at reflux for 2 hr. while water is removed by azeotropic distillation. The resulting green liquid is used without further purification.

The above procedure is suitable for use in preparing silicon naphthalocyanine-di-[pentadecyl(ethylene glycol) mono-1-ethylnaphthalene ether]; silicon naphthalocyanine-di-[pentadecyl(ethyleneglycol) mono-1-methylanthracene ether); and 1:3 Silicon(VI) phthalo/naphthalocyanine-di-[pentadecyl(ethylene glycol) mono-1-ethylnaphthalene ether]. The cleaning compositions provided in accordance with this invention may be in the form of granules, liquids, bars, and the like, and typically are formulated to provide an in-use pH in the range of 9 to 11, however in the case of non-aqueous or low aqueous compositions the pH ranges may vary outside this range. Various carriers such as sodium sulfate, water, water-ethanol, BPP, MPP, EPP, PPP, sodium carbonate, and the like, may be used routinely to formulate the finished products. Granules may be produced by spray-drying or by agglomeration, using known techniques, to provide products in the density range of 350–950 g/l. Bars may be formulated using conventional extrusion techniques. The compositions may also contain conventional perfumes, bactericides, hydrotropes and the like. In the case of non-aqueous or low aqueous compositions, the cleaning compositions may be applied to an article which is used to deliver the compositions of the present invention to a fabric or to a hard surface. Non-limiting examples of compositions according to this invention are as follows:

|  | weight % | | | |
| --- | --- | --- | --- | --- |
| Ingredients | 21 | 22 | 23 | 24 |
| Sodium LAS | 15 | 30 | 20 | 25 |
| NEODOL | 1 | 1 | 1 | 1 |
| Alkyl Dimethyl Ammonium Chloride | 0.5 | 1 | 0.5 | 0.7 |
| Sodium Tripolyphosphate | 15 | 35 | 22 | 28 |
| Sodium Carbonate | 10 | 10 | 15 | 15 |
| SOKALAN | 2 | 2 | 2 | 2 |
| Carboxymethyl Cellulose | 1 | 1 | 1 | 1 |
| Tinopal CBS-X | 0.1 | 0.1 | 0.1 | 0.1 |
| Soil Release Agent[1] | 0.2 | 0.2 | 0.3 | 0.3 |
| Savinase 6.0T | 0.3 | 0.6 | 0.5 | 0.6 |
| BAN 300T | 0.2 | 0.5 | 0.5 | 0.6 |
| Lipolase 100T | 0.1 | 0.2 | 0.2 | 0.3 |
| CAREZYME 5T | 0.1 | 0.2 | 0.2 | 0.3 |
| Sodium Perborate | — | — | 3.0 | 5.0 |
| NOBS | — | — | 2.0 | 3.0 |
| Photobleach[2] (ppm) | 0.005 | 0.01 | 0.008 | 0.01 |
| Moisture + SodiumSulfate + Perfume + Miscellaneous | Balance | Balance | Balance | Balance |

[1]Soil Release Agent according to U.S. Pat. No. 5,415,807 Gosselink et al., issued May 16, 1995.
[2]Photobleach according to Example 7.

What is claimed is:
1. A singlet oxygen generator having the formula:

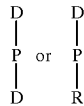

wherein P is a photosensitizer unit having the formula:

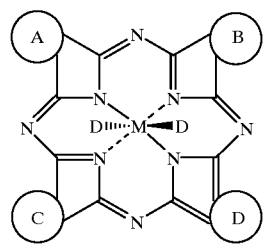

or the formula:

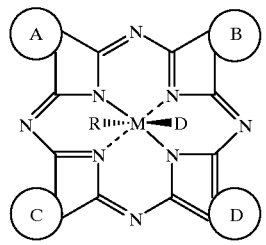

wherein M is a photoactive metal or non-metal having a valence greater than or equal to 3 which is selected from the group consisting of silicon, phosphorous, palladium, platinum, lead, germanium, tin, and mixtures thereof; rings A, B, C, and D are aromatic rings, wherein each of said rings A, B, C, and D are each independently:

i) a benzene ring unit having the formula:

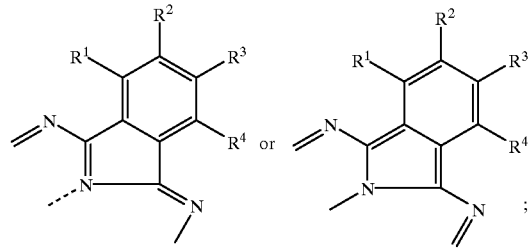

ii) a 2,3-naphthylene ring unit having the formula:

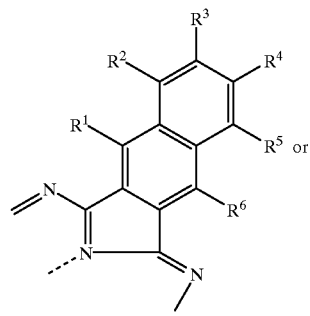

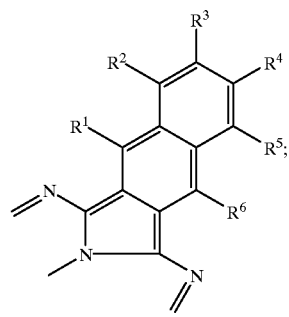

iii) a 1,2-naphthylene ring unit having the formula:

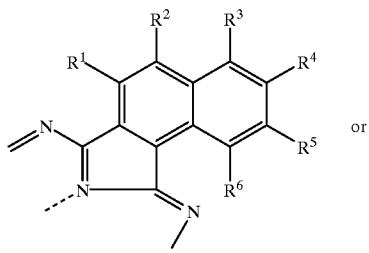

or

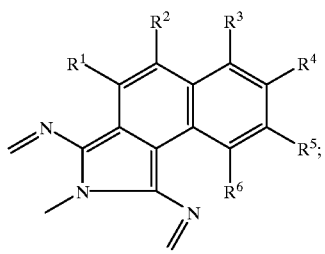

iv) an anthracene ring unit having the formula:

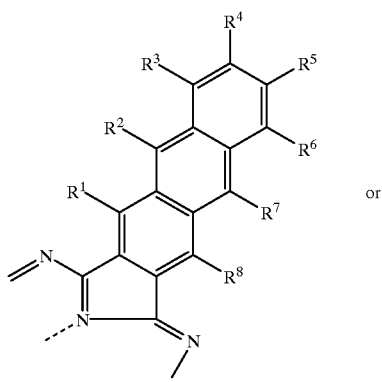

or

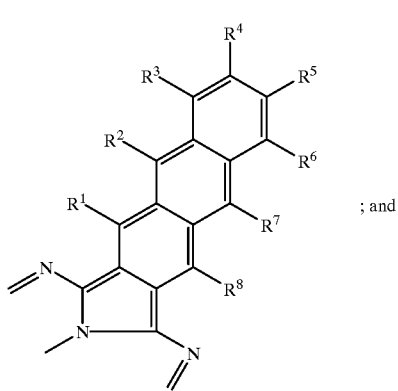

; and v) an phenanthrene ring unit having the formula:

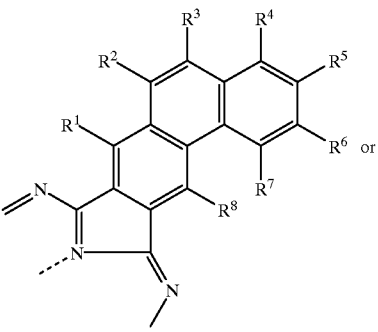

or

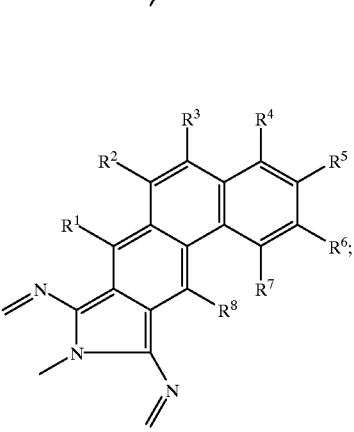

;

wherein each $R^1$, $R^2$, $R^3$, $R^4$, $R^5$, $R^6$, $R^7$, and $R^8$ unit is independently selected from the group consisting of:
a) hydrogen;
b) halogen;
c) hydroxy;
d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) polyhydroxyl substituted $C_3$–$C_{22}$ alkyl;
g) $C_1$–$C_{22}$ alkoxy;
h) branched alkoxy having the formula:

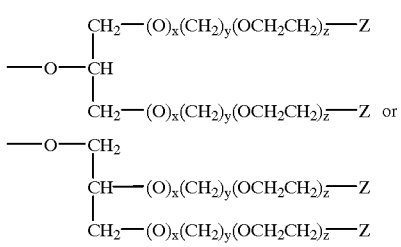

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, $OPO_3^{2-}M$, or mixtures thereof; M is a water soluble cation in sufficient amount to satisfy charge balance;
x is 0 or 1, each y independently has the value from 0 to 6, each z independently has the value from 0 to 100;

i) substituted aryl, unsubstituted aryl, or mixtures thereof;

j) substituted alkylenearyl, unsubstituted alkylenearyl, or mixtures thereof;

k) substituted aryloxy, unsubstituted aryloxy, or mixtures thereof;

l) substituted oxyalkylenearyl, unsubstituted oxyalkylenearyl, or mixtures thereof;

m) substituted alkyleneoxyaryl, unsubstituted alkyleneoxyaryl, or mixtures thereof;

n) $C_1$–$C_{22}$ thioalkyl, $C_3$–$C_{22}$ branched thioalkyl, or mixtures thereof;

o) an ester of the formula —$CO_2R^9$ wherein $R^9$ is
  i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  iii) polyhydroxyl substituted $C_3$–$C_{22}$ alkylene;
  iv) $C_3$–$C_{22}$ glycol;
  v) $C_1$–$C_{22}$ alkoxy;
  vi) $C_3$–$C_{22}$ branched alkoxy;
  vii) substituted aryl, unsubstituted aryl, or mixtures thereof;
  viii) substituted alkylenearyl, unsubstituted alkylenearyl, or mixtures thereof;
  ix) substituted aryloxy, unsubstituted aryloxy, or mixtures thereof;
  x) substituted oxyalkylenearyl, unsubstituted oxyalkylenearyl, or mixtures thereof;
  xi) substituted alkyleneoxyaryl, unsubstituted alkyleneoxyaryl, or mixtures thereof;

p) an alkyleneamino unit of the formula:

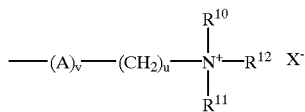

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
$R^{12}$ is:
  i) hydrogen;
  ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
    A is nitrogen or oxygen; X is chlorine, bromine, iodine, or other water soluble anion, v is 0 or 1, u is from 0 to 22;

q) an amino unit of the formula:

wherein $R^{17}$ and $R^{18}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

r) an alkylethyleneoxy unit of the formula:

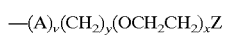

wherein Z is:
  i) hydrogen;
  ii) hydroxyl;
  iii) —$CO_2H$;
  iv) —$SO_3^-M^+$;
  v) —$OSO_3^-M^+$;
  vi) $C_1$–$C_6$ alkoxy;
  vii) substituted aryl, unsubstituted aryl, or mixtures thereof;
  viii) substituted aryloxy, unsubstituted aryloxy, or mixtures thereof;
  ix) alkyleneamino; or mixtures thereof;
    A is nitrogen or oxygen, M is a water soluble cation, v is 0 or 1, x is from 0 to 100, y is from 0 to 12;

s) substituted siloxy of the formula:

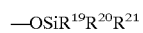

wherein each $R^{19}$, $R^{20}$, and $R^{21}$ is independently
  i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  ii) substituted aryl, unsubstituted aryl, or mixtures thereof;
  iii) substituted aryloxy, unsubstituted aryloxy, or mixtures thereof;
  iv) an alkylethyleneoxy unit of the formula:

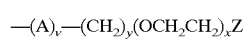

wherein Z is:
  a) hydrogen;
  b) hydroxyl;
  c) —$CO_2H$;
  d) —$SO_3^-M^+$;
  e) —$OSO_3^-M^+$;
  f) $C_1$–$C_6$ alkoxy;
  g) substituted aryl, unsubstituted aryl, or mixtures thereof;
  h) substituted aryloxy, unsubstituted aryloxy, or mixtures thereof;
  i) alkyleneamino; or mixtures thereof;
    A is nitrogen or oxygen, M is a water soluble cation, v is 0 or 1, x is from 0 to 100, y is from 0 to 12;
    and mixtures thereof;

R is an axial moiety which mediates the solubility or substantivity of the singlet oxygen generator wherein R is selected from:
a) hydrogen;
b) halogen;
c) hydroxy;
d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) polyhydroxyl substituted $C_3$–$C_{22}$ alkyl;
g) $C_1$–$C_{22}$ alkoxy;

h) branched alkoxy having the formula:

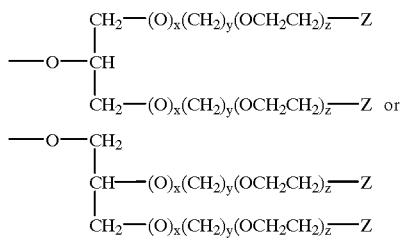

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, $PO_3^{2-}M$, —$OPO_3^{2-}M$, or mixtures thereof; M is a water soluble cation in sufficient amount to satisfy charge balance; x is 0 or 1, each y independently has the value from 0 to 6, each z independently has the value from 0 to 100;

i) substituted aryl, unsubstituted aryl, or mixtures thereof;

j) substituted alkylenearyl, unsubstituted alkylenearyl, or mixtures thereof;

k) substituted aryloxy, unsubstituted aryloxy, or mixtures thereof;

l) substituted oxyalkylenearyl, unsubstituted oxyalkylenearyl, or mixtures thereof;

m) substituted alkyleneoxyaryl, unsubstituted alkyleneoxyaryl, or mixtures thereof;

n) $C_1$–$C_{22}$ thioalkyl, $C_3$–$C_{22}$ branched thioalkyl, or mixtures thereof;

o) a carboxylate of the formula:

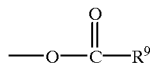

wherein $R^9$ is:
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
iii) polyhydroxyl substituted $C_3$–$C_{22}$ alkylene;
iv) $C_3$–$C_{22}$ glycol;
v) $C_1$–$C_{22}$ alkoxy;
vi) $C_3$–$C_{22}$ branched alkoxy;
vii) substituted aryl, unsubstituted aryl, or mixtures thereof;
viii) substituted alkylenearyl, unsubstituted alkylenearyl, or mixtures thereof;
ix) substituted aryloxy, unsubstituted aryloxy, or mixtures thereof;
x) substituted oxyalkylenearyl, unsubstituted oxyalkylenearyl, or mixtures thereof;
xi) substituted alkyleneoxyaryl, unsubstituted alkyleneoxyaryl, or mixtures thereof;

p) an alkyleneamino unit of the formula:

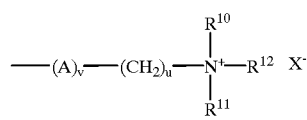

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
$R^{12}$ is:
i) hydrogen;
ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
A is nitrogen or oxygen; X is chlorine, bromine, iodine, or other water soluble anion, v is 0 or 1, u is from 0 to 22;

q) an amino unit of the formula:

wherein $R^{17}$ and $R^{18}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

r) an alkylethyleneoxy unit of the formula:

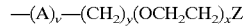

wherein Z is:
i) hydrogen;
ii) hydroxyl;
iii) —$CO_2H$;
iv) —$SO_3^-M^+$;
v) —$OSO_3^-M^+$;
vi) $C_1$–$C_6$ alkoxy;
vii) substituted aryl, unsubstituted aryl, or mixtures thereof;
viii) substituted aryloxy, unsubstituted aryloxy, or mixtures thereof;
ix) alkyleneamino; or mixtures thereof;
A is nitrogen or oxygen, M is a water soluble cation, v is 0 or 1, x is from 0 to 100, y is from 0 to 12;

s) substituted siloxy of the formula:

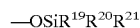

wherein each $R^{19}$, $R^{20}$, and $R^{21}$ is independently
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) substituted aryl, unsubstituted aryl, or mixtures thereof;
iii) substituted aryloxy, unsubstituted aryloxy, or mixtures thereof;
iv) an alkylethyleneoxy unit of the formula:

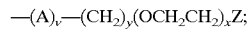

wherein Z is:
a) hydrogen;
b) hydroxyl;
c) —$CO_2H$;
d) —$SO_3^-M^+$;
e) —$OSO_3^-M^+$;
f) $C_1$–$C_6$ alkoxy;
g) substituted aryl, unsubstituted aryl, or mixtures thereof;

h) substituted aryloxy, unsubstituted aryloxy, or mixtures thereof;
i) alkyleneamino; or mixtures thereof;

A is nitrogen or oxygen, M is a water soluble cation, v is 0 or 1, x is from 0 to 100, y is from 0 to 12;

and mixtures thereof; and D is a unit which increases the efficiency of singlet oxygen production, said unit having the formula

or

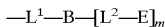

wherein E is an aromatic unit, provided said E aromatic unit:
a) absorbs ultra violet radiation at a wavelength of from about 200 nm to about 400 nm;
b) has an extinction coefficient of at least about 100; and
c) has a fluorescence spectrum which overlaps the absorption band of said photosensitizer unit;

B is a branching unit; and $L^1$ and $L^2$ are linking units, provided said linking units when taken together with said B unit comprise a total of at least 20 continuous covalent bonds from said P unit to said E units; m is from 2 to 4.

2. A compound according to claim 1 wherein $L^1$ and $L^2$ are independently selected from the group consisting of oxygen, linear or branched alkylene, linear or branched alkenylene; linear or branched alkyleneoxy, substituted or unsubstituted arylene, substituted or unsubstituted alkylenearylene, substituted or unsubstituted aryleneoxy, substituted or unsubstituted oxyalkylenearylene, substituted or unsubstituted alkyleneoxyarylene, and mixtures thereof.

3. A compound according to claim 1 wherein the branching unit B has the formula:

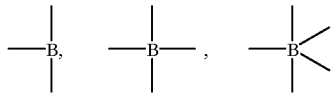

wherein B is selected from the group consisting of boron, aluminum, nitrogen, phosphorous, carbon, silicon, tin, germanium, and mixtures thereof.

4. A compound according to claim 1 wherein the E unit has an extinction coefficient of at least 1000.

5. A compound according to claim 4 wherein the E unit has an extinction coefficient of at least 10,000.

6. A laundry detergent composition comprising:
a) from about 0.1%, to about 20% by weight, of a detersive surfactant;
b) from about 0.001 ppm to about 1000 ppm, of a singlet oxygen generator as set forth in claim 1; and
c) the balance carriers and adjunct ingredients.

7. A composition according to claim 6 wherein the detersive surfactant is selected from the group consisting of anionic, cationic, nonionic, zwitterionic, ampholytic surfactants, and mixtures thereof.

8. A composition according to claim 6 wherein the adjunct ingredients are members selected from the group consisting of buffers, builders, chelants, filler salts, soil release agents, dispersants, enzymes, enzyme boosters, perfumes, thickeners, abrasives, solvents, clays, and mixtures thereof.

9. A composition according to claim 6 wherein the E unit has an extinction coefficient of at least 1000.

10. A composition according to claim 9 wherein the E unit has an extinction coefficient of at least 10,000.

11. A method for cleaning a stained fabric comprising contacting a stained fabric in need of cleaning with an aqueous cleaning solution comprising at least 0.01% of the singlet oxygen generator according to claim 1 followed by exposing the surface of the treated fabric to a source of light having a minimal wavelength range from about 300 to about 1200 nanometers.

12. A method for cleaning a hard surface comprising contacting a hard surface in need of cleaning with an aqueous cleaning composition comprising at least 0.001 ppm of the singlet oxygen generator according to claim 1 and exposing the hard surface to a source of light having a minimal wavelength range from about 300 to about 1200 nanometers.

13. A method for generating oxygen comprising exposing a singlet oxygen generator according to claim 1 to a source of light having a minimal wavelength range from about 300 to about 1200 nanometers.

14. A singlet oxygen generator having the formula:

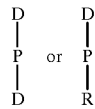

wherein P is a photosensitizer unit having the formula:

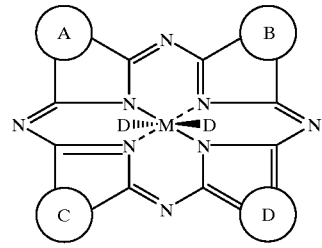

or the formula:

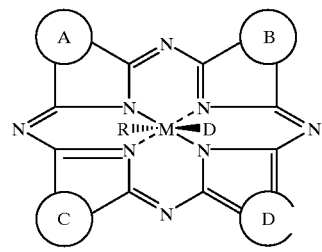

wherein M is a photoactive metal or non-metal having a valence greater than or equal to 3 which is selected from the group consisting of silicon, phosphorous, palladium, platinum, lead, germanium, tin, and mixtures thereof; rings A, B, C, and D are aromatic rings, wherein each of said rings A, B, C, and D are each independently:

i) a benzene ring unit having the formula:

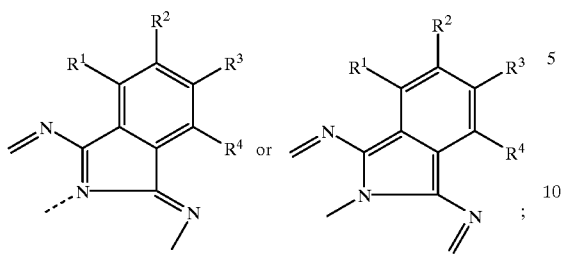

ii) a 2,3-naphthylene ring unit having the formula:

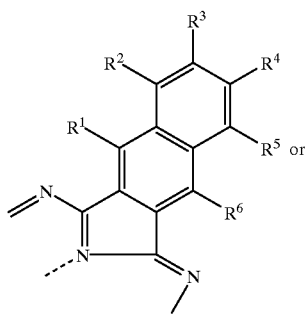

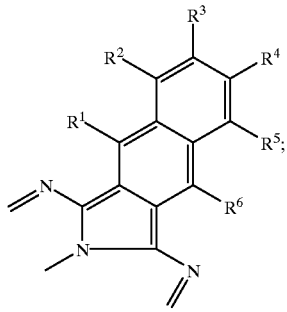

iii) a 1,2-naphthylene ring unit having the formula:

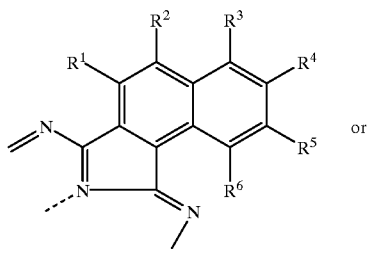

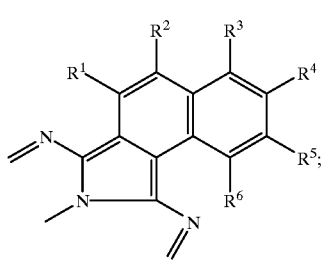

iv) an anthracene ring unit having the formula:

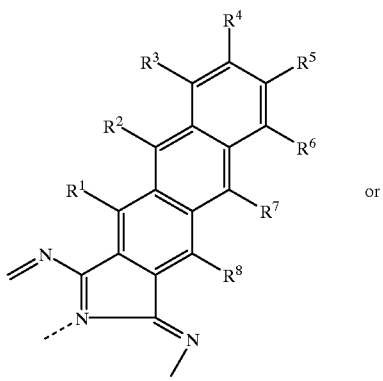

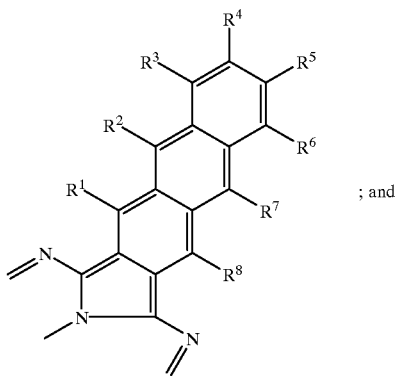

v) an phenanthrene ring unit having the formula:

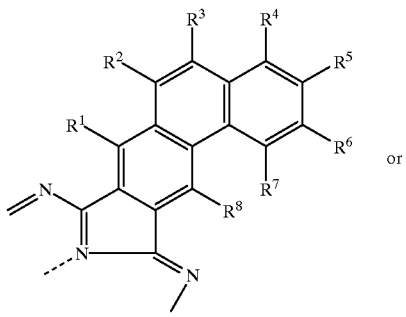

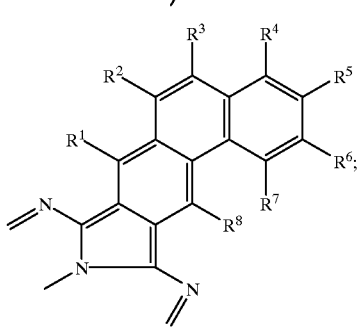

wherein each $R^1$, $R^2$, $R^3$, $R^4$, $R^5$, $R^6$, $R^7$, and $R^8$ unit is independently selected from the group consisting of:
a) hydrogen;
b) halogen;
c) hydroxy;

43 d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) polyhydroxyl substituted $C_3$–$C_{22}$ alkyl;
g) $C_1$–$C_{22}$ alkoxy;
h) branched alkoxy having the formula:

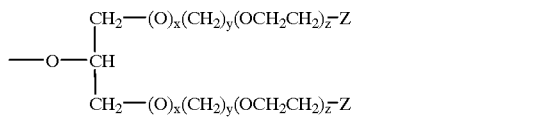

or

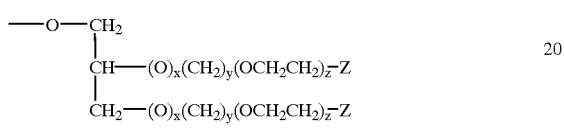

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, or mixtures thereof; M is a water soluble cation in sufficient amount to satisfy charge balance;
x is 0 or 1, each y independently has the value from 0 to 6, each z independently has the value from 0 to 100;
i) substituted aryl, unsubstituted aryl, or mixtures thereof;
j) substituted alkylenearyl, unsubstituted alkylenearyl, or mixtures thereof;
k) substituted aryloxy, unsubstituted aryloxy, or mixtures thereof;
l) substituted oxyalkylenearyl, unsubstituted oxyalkylenearyl, or mixtures thereof;
m) substituted alkyleneoxyaryl, unsubstituted alkyleneoxyaryl, or mixtures thereof;
n) $C_1$–$C_{22}$ thioalkyl, $C_3$–$C_{22}$ branched thioalkyl, or mixtures thereof;
o) an ester of the formula —$CO_2R^9$ wherein $R^9$ is
   i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
   ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
   iii) polyhydroxyl substituted $C_3$–$C_{22}$ alkylene;
   iv) $C_3$–$C_{22}$ glycol;
   v) $C_1$–$C_{22}$ alkoxy;
   vi) $C_3$–$C_{22}$ branched alkoxy;
   vii) substituted aryl, unsubstituted aryl, or mixtures thereof;
   viii) substituted alkylenearyl, unsubstituted alkylenearyl, or mixtures thereof;
   ix) substituted aryloxy, unsubstituted aryloxy, or mixtures thereof;
   x) substituted oxyalkylenearyl, unsubstituted oxyalkylenearyl, or mixtures thereof;
   xi) substituted alkyleneoxyaryl, unsubstituted alkyleneoxyaryl, or mixtures thereof;

44 p) an alkyleneamino unit of the formula:

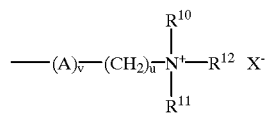

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
$R^{12}$ is:
   i) hydrogen;
   ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
   A is nitrogen or oxygen; X is chlorine, bromine, iodine, or other water soluble anion, v is 0 or 1, u is from 0 to 22;
q) an amino unit of the formula:

—$NR^{17}R^{18}$ wherein $R^{17}$ and $R^{18}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
r) an alkylethyleneoxy unit of the formula:

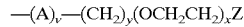

wherein Z is:
   i) hydrogen;
   ii) hydroxyl;
   iii) —$CO_2H$;
   iv) —$SO_3^-M^+$;
   v) —$OSO_3^-M^+$;
   vi) $C_1$–$C_6$ alkoxy;
   vii) substituted aryl, unsubstituted aryl, or mixtures thereof;
   viii) substituted aryloxy, unsubstituted aryloxy, or mixtures thereof;
   ix) alkyleneamino; or mixtures thereof;
   A is nitrogen or oxygen, M is a water soluble cation, v is 0 or 1, x is from 0 to 100, y is from 0 to 12;
s) substituted siloxy of the formula:

—$OSiR^{19}R^{20}R^{21}$ wherein each $R^{19}$, $R^{20}$, and $R^{21}$ is independently
   i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
   ii) substituted aryl, unsubstituted aryl, or mixtures thereof;
   iii) substituted aryloxy, unsubstituted aryloxy, or mixtures thereof;
   iv) an alkylethyleneoxy unit of the formula:

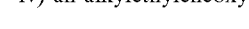

wherein Z is:
   a) hydrogen;
   b) hydroxyl;
   c) —$CO_2H$;
   d) —$SO_3^-M^+$;
   e) —$OSO_3^-M^+$;
   f) $C_1$–$C_6$ alkoxy;
   g) substituted aryl, unsubstituted aryl, or mixtures thereof;

h) substituted aryloxy, unsubstituted aryloxy, or mixtures thereof;
i) alkyleneamino; or mixtures thereof;

A is nitrogen or oxygen, M is a water soluble cation, v is 0 or 1, x is from 0 to 100, y is from 0 to 12;

and mixtures thereof;

R is an axial moiety which mediates the solubility or substantivity of the singlet oxygen generator wherein R is selected from:
a) hydrogen;
b) halogen;
c) hydroxy;
d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) polyhydroxyl substituted $C_3$–$C_{22}$ alkyl;
g) $C_1$–$C_{22}$ alkoxy;
h) branched alkoxy having the formula:

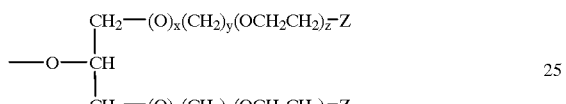

or

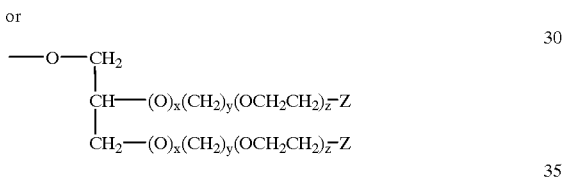

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, or mixtures thereof; M is a water soluble cation in sufficient amount to satisfy charge balance; x is 0 or 1, each y independently has the value from 0 to 6, each z independently has the value from 0 to 100;
i) substituted aryl, unsubstituted aryl, or mixtures thereof;
j) substituted alkylenearyl, unsubstituted alkylenearyl, or mixtures thereof;
k) substituted aryloxy, unsubstituted aryloxy, or mixtures thereof;
l) substituted oxyalkylenearyl, unsubstituted oxyalkylenearyl, or mixtures thereof;
m) substituted alkyleneoxyaryl, unsubstituted alkyleneoxyaryl, or mixtures thereof;
n) $C_1$–$C_{22}$ thioalkyl, $C_3$–$C_{22}$ branched thioalkyl, or mixtures thereof;
o) a carboxylate of the formula:

wherein $R^9$ is:
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
iii) polyhydroxyl substituted $C_3$–$C_{22}$ alkylene;
iv) $C_3$–$C_{22}$ glycol;
v) $C_1$–$C_{22}$ alkoxy;
vi) $C_3$–$C_{22}$ branched alkoxy;
vii) substituted aryl, unsubstituted aryl, or mixtures thereof;
viii) substituted alkylenearyl, unsubstituted alkylenearyl, or mixtures thereof;
ix) substituted aryloxy, unsubstituted aryloxy, or mixtures thereof;
x) substituted oxyalkylenearyl, unsubstituted oxyalkylenearyl, or mixtures thereof;
xi) substituted alkyleneoxyaryl, unsubstituted alkyleneoxyaryl, or mixtures thereof;
p) an alkyleneamino unit of the formula:

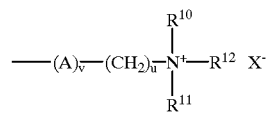

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
$R^{12}$ is:
i) hydrogen;
ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

A is nitrogen or oxygen; X is chlorine, bromine, iodine, or other water soluble anion, v is 0 or 1, u is from 0 to 22;
q) an amino unit of the formula:

wherein $R^{17}$ and $R^{18}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
r) an alkylethyleneoxy unit of the formula:

—$(A)_v$—$(CH_2)_y(OCH_2CH_2)_xZ$ wherein Z is:
i) hydrogen;
ii) hydroxyl;
iii) —$CO_2H$;
iv) —$SO_3^-M^+$;
v) —$OSO_3^-M^+$;
vi) $C_1$–$C_6$ alkoxy;
vii) substituted aryl, unsubstituted aryl, or mixtures thereof;
viii) substituted aryloxy, unsubstituted aryloxy, or mixtures thereof;
ix) alkyleneamino; or mixtures thereof;

A is nitrogen or oxygen, M is a water soluble cation, v is 0 or 1, x is from 0 to 100, y is from 0 to 12;
s) substituted siloxy of the formula:

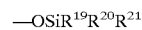

wherein each $R^{19}$, $R^{20}$, and $R^{21}$ is independently
i) $C_1$–$C_{22}$ alkyl $C_3$–$C_{22}$ branched alkyl, $C_2$–$C_{22}$ alkenyl, $C_3$–$C_{22}$ branched alkenyl, or mixtures thereof;
ii) substituted aryl, unsubstituted aryl, or mixtures thereof;
iii) substituted aryloxy, unsubstituted aryloxy, or mixtures thereof;

iv) an alkylethyleneoxy unit of the formula:

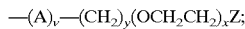—(A)$_v$—(CH$_2$)$_y$(OCH$_2$CH$_2$)$_x$Z;

wherein Z is:
a) hydrogen;
b) hydroxyl;
c) —CO$_2$H;
d) —SO$_3^-$M$^+$;
e) —OSO$_3^-$M$^+$;
f) C$_1$–C$_6$ alkoxy;
g) substituted aryl, unsubstituted aryl, or mixtures thereof;
h) substituted aryloxy, unsubstituted aryloxy, or mixtures thereof;
i) alkyleneamino; or mixtures thereof;
A is nitrogen or oxygen, M is a water soluble cation, v is 0 or 1, x is from 0 to 100, y is from 0 to 12;

and mixtures thereof; and D is a unit which increases the efficiency of singlet oxygen production, said unit having the formula

—L$^1$—E or

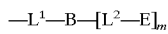—L$^1$—B—[L$^2$—E]$_m$ wherein E is an aromatic unit having six carbon atoms, provided said E aromatic unit:
a) absorbs ultra violet radiation at a wavelength of from about 200 nm to about 400 nm;
b) has an extinction coefficient of at least about 100; and
c) has a fluorescence spectrum which overlaps the absorption band of said photosensitizer unit;

B is a branching unit; and L$^1$ and L$^2$ are linking units, provided said linking units when taken together with said B unit comprise a total of at least 20 continuous covalent bonds from said P unit to said E units; m is from 2 to 4.

15. A singlet oxygen generator having the formula:

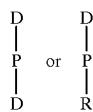

wherein P is a photosensitizer unit having the formula:

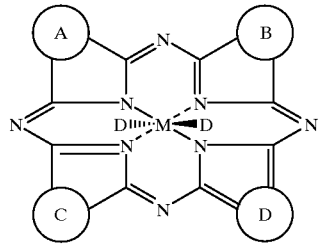

or the formula:

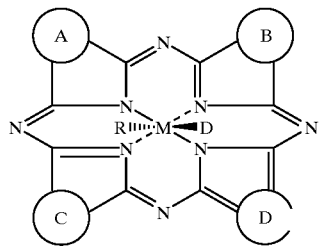

wherein M is a photoactive metal or non-metal having a valence greater than or equal to 3 which is selected from the group consisting of silicon, phosphorous, palladium, platinum, lead, germanium, tin, and mixtures thereof, rings A, B, C, and D are aromatic rings, wherein each of said rings A, B, C, and D are each independently:

i) a benzene ring unit having the formula:

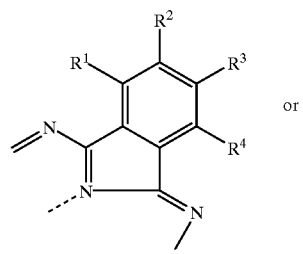

or

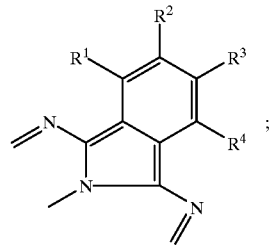

ii) a 2,3-naphthylene ring unit having the formula:

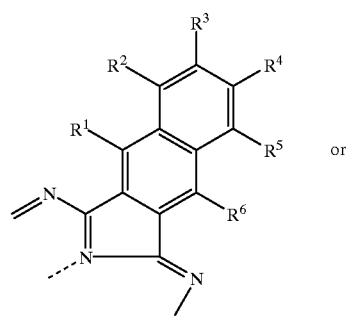

or

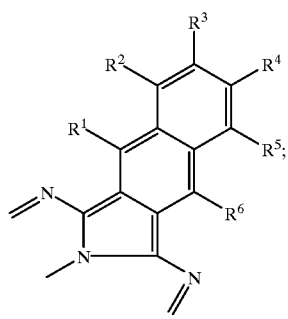

iii) a 1,2-naphthylene ring unit having the formula:

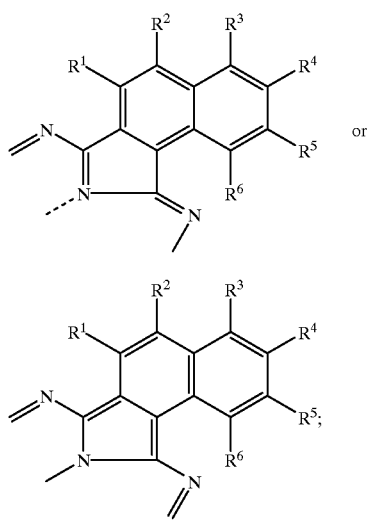

iv) an anthracene ring unit having the formula:

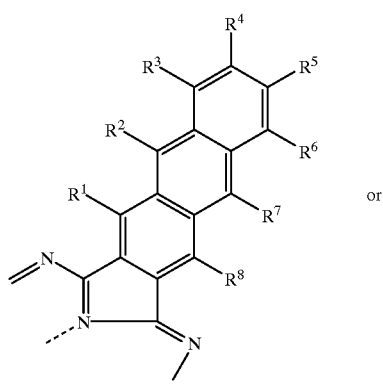

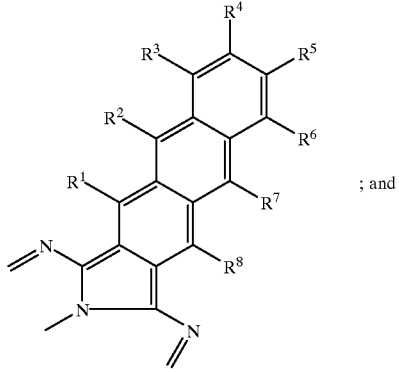

v) an phenanthrene ring unit having the formula:

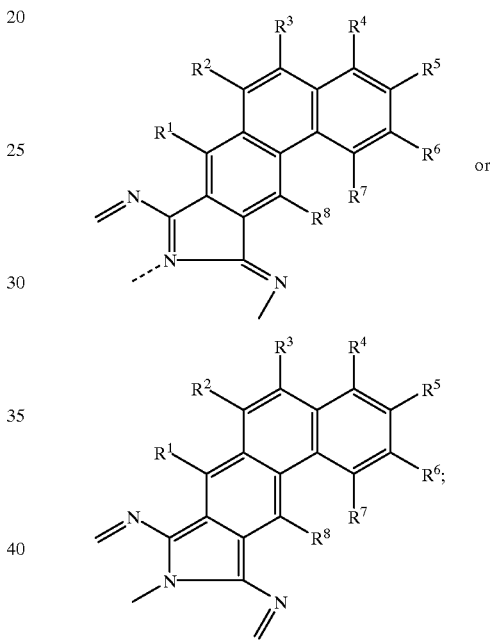

wherein each $R^1$, $R^2$, $R^3$, $R^4$, $R^5$, $R^6$, $R^7$, and $R^8$ unit is independently selected from the group consisting of:
a) hydrogen;
b) halogen;
c) hydroxy;
d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) polyhydroxyl substituted $C_3$–$C_{22}$ alkyl;
g) $C_1$–$C_{22}$ alkoxy;

h) branched alkoxy having the formula:

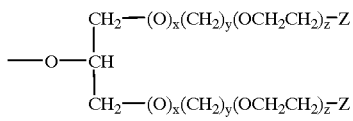

or

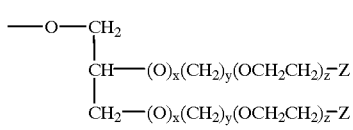

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, or mixtures thereof; M is a water soluble cation in sufficient amount to satisfy charge balance;
x is 0 or 1, each y independently has the value from 0 to 6, each z independently has the value from 0 to 100;
i) substituted aryl, unsubstituted aryl, or mixtures thereof;
j) substituted alkylenearyl, unsubstituted alkylenearyl, or mixtures thereof;
k) substituted aryloxy, unsubstituted aryloxy, or mixtures thereof;
l) substituted oxyalkylenearyl, unsubstituted oxyalkylenearyl, or mixtures thereof;
m) substituted alkyleneoxyaryl, unsubstituted alkyleneoxyaryl, or mixtures thereof;
n) an ester of the formula —$CO_2R^9$ wherein $R^9$ is
  i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  iii) polyhydroxyl substituted $C_3$–$C_{22}$ alkylene;
  iv) $C_3$–$C_{22}$ glycol;
  v) $C_1$–$C_{22}$ alkoxy;
  vi) $C_3$–$C_{22}$ branched alkoxy;
  vii) substituted aryl, unsubstituted aryl, or mixtures thereof;
  viii) substituted alkylenearyl, unsubstituted alkylenearyl, or mixtures thereof;
  ix) substituted aryloxy, unsubstituted aryloxy, or mixtures thereof;
  x) substituted oxyalkylenearyl, unsubstituted oxyalkylenearyl, or mixtures thereof;
  xi) substituted alkyleneoxyaryl, unsubstituted alkyleneoxyaryl, or mixtures thereof;
o) an alkyleneamino unit of the formula:

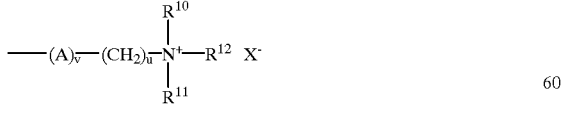

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
$R^{12}$ is:
  i) hydrogen;
  ii) $C_1C_{22}$ alkyl, $C_3$–$C_{22}$ branched alkyl, $C_2$–$C_{22}$ alkenyl, $C_3$–$C_{22}$ branched alkenyl, or mixtures thereof;
  A is nitrogen or oxygen; X is chlorine, bromine, iodine, or other water soluble anion, v is 0 or 1, u is from 0 to 22;
p) an amino unit of the formula:

wherein $R^{17}$ and $R^{18}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
q) an alkylethyleneoxy unit of the formula:

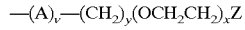

wherein Z is:
  i) hydrogen;
  ii) hydroxyl;
  iii) —$CO_2H$;
  iv) —$SO_3^-M^+$;
  v) —$OSO_3^-M^+$;
  vi) $C_1$–$C_6$ alkoxy;
  vii) substituted aryl, unsubstituted aryl, or mixtures thereof;
  viii) substituted aryloxy, unsubstituted aryloxy, or mixtures thereof;
  ix) alkyleneamino; or mixtures thereof;
  A is nitrogen or oxygen, M is a water soluble cation, v is 0 or 1, x is from 0 to 100, y is from 0 to 12;
r) substituted siloxy of the formula:

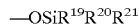

wherein each $R^{19}$, $R^{20}$, and $R^{21}$ is independently
  i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  ii) substituted aryl, unsubstituted aryl, or mixtures thereof;
  iii) substituted aryloxy, unsubstituted aryloxy, or mixtures thereof;
  iv) an alkylethyleneoxy unit of the formula:

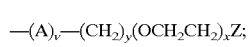

wherein Z is:
    a) hydrogen;
    b) hydroxyl;
    c) —$CO_2H$;
    d) —$SO_3^-M^+$;
    e) —$OSO_3^-M^+$;
    f) $C_1$–$C_6$ alkoxy;
    g) substituted aryl, unsubstituted aryl, or mixtures thereof;
    h) substituted aryloxy, unsubstituted aryloxy, or mixtures thereof;
    i) alkyleneamino; or mixtures thereof;
    A is nitrogen or oxygen, M is a water soluble cation, v is 0 or 1, x is from 0 to 100, y is from 0 to 12;
  and mixtures thereof;
R is an axial moiety which mediates the solubility or substantivity of the singlet oxygen generator wherein R is selected from:
  a) hydrogen;
  b) halogen;
  c) hydroxy;

d) $C_1-C_{22}$ alkyl, $C_3-C_{22}$ branched alkyl, $C_2-C_{22}$ alkenyl, $C_3-C_{22}$ branched alkenyl, or mixtures thereof;
e) halogen substituted $C_1-C_{22}$ alkyl, $C_3-C_{22}$ branched alkyl, $C_2-C_{22}$ alkenyl, $C_3-C_{22}$ branched alkenyl, or mixtures thereof;
f) polyhydroxyl substituted $C_3-C_{22}$ alkyl;
g) $C_1-C_{22}$ alkoxy;
h) branched alkoxy having the formula:

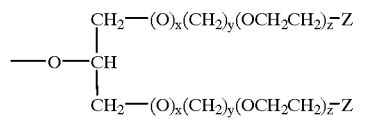

or

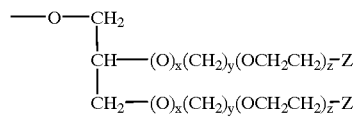

wherein Z is hydrogen, hydroxyl, $C_1-C_{30}$ alkyl, $C_1-C_{30}$ alkoxy, $-CO_2H$, $-OCH_2CO_2H$, $-SO_3^-M^+$, $-OSO_3^-M^+$, $-PO_3^{2-}M$, $-OPO_3^{2-}M$, or mixtures thereof; M is a water soluble cation in sufficient amount to satisfy charge balance; x is 0 or 1, each y independently has the value from 0 to 6, each z independently has the value from 0 to 100;
i) substituted aryl, unsubstituted aryl, or mixtures thereof;
j) substituted alkylenearyl, unsubstituted alkylenearyl, or mixtures thereof;
k) substituted aryloxy, unsubstituted aryloxy, or mixtures thereof;
l) substituted oxyalkylenearyl, unsubstituted oxyalkylenearyl, or mixtures thereof;
m) substituted alkyleneoxyaryl, unsubstituted alkyleneoxyaryl, or mixtures thereof;
n) $C_1-C_{22}$ thioalkyl, $C_3-C_{22}$ branched thioalkyl, or mixtures thereof;
o) a carboxylate of the formula:

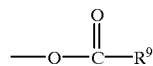

wherein $R^9$ is:
i) $C_1-C_{22}$ alkyl, $C_3-C_{22}$ branched alkyl, $C_2-C_{22}$ alkenyl, $C_3-C_{22}$ branched alkenyl, or mixtures thereof;
ii) halogen substituted $C_1-C_{22}$ alkyl, $C_3-C_{22}$ branched alkyl, $C_2-C_{22}$ alkenyl, $C_3-C_{22}$ branched alkenyl, or mixtures thereof;
iii) polyhydroxyl substituted $C_3-C_{22}$ alkylene;
iv) $C_3-C_{22}$ glycol;
v) $C_1-C_{22}$ alkoxy;
vi) $C_3-C_{22}$ branched alkoxy;
vii) substituted aryl, unsubstituted aryl, or mixtures thereof;
viii) substituted alkylenearyl, unsubstituted alkylenearyl, or mixtures thereof;
ix) substituted aryloxy, unsubstituted aryloxy, or mixtures thereof;
x) substituted oxyalkylenearyl, unsubstituted oxyalkylenearyl, or mixtures thereof;
xi) substituted alkyleneoxyaryl, unsubstituted alkyleneoxyaryl, or mixtures thereof;
p) an alkyleneamino unit of the formula:

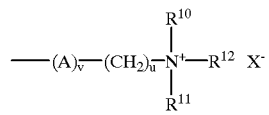

wherein $R^{10}$ and $R^{11}$ are $C_1-C_{22}$ alkyl, $C_3-C_{22}$ branched alkyl, $C_2-C_{22}$ alkenyl, $C_3-C_{22}$ branched alkenyl, or mixtures thereof;
$R^{12}$ is:
i) hydrogen;
ii) $C_1-C_{22}$ alkyl, $C_3-C_{22}$ branched alkyl, $C_2-C_{22}$ alkenyl, $C_3-C_{22}$ branched alkenyl, or mixtures thereof;
A is nitrogen or oxygen; X is chlorine, bromine, iodine, or other water soluble anion, v is 0 or 1, u is from 0 to 22;
q) an amino unit of the formula:

wherein $R^{17}$ and $R^{18}$ are $C_1-C_{22}$ alkyl, $C_3-C_{22}$ branched alkyl, $C_2-C_{22}$ alkenyl, $C_3-C_{22}$ branched alkenyl, or mixtures thereof;
r) an alkylethyleneoxy unit of the formula:

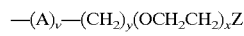

wherein Z is:
i) hydrogen;
ii) hydroxyl;
iii) $-CO_2H$;
iv) $-SO_3^-M^+$;
v) $-OSO_3^-M^+$;
vi) $C_1-C_6$ alkoxy;
vii) substituted aryl, unsubstituted aryl, or mixtures thereof;
viii) substituted aryloxy, unsubstituted aryloxy, or mixtures thereof;
ix) alkyleneamino; or mixtures thereof;
A is nitrogen or oxygen, M is a water soluble cation, v is 0 or 1, x is from 0 to 100, y is from 0 to 12;
s) substituted siloxy of the formula:

wherein each $R^{19}$, $R^{20}$, and $R^{21}$ is independently
i) $C_1-C_{22}$ alkyl, $C_3-C_{22}$ branched alkyl, $C_2-C_{22}$ alkenyl, $C_3-C_{22}$ branched alkenyl, or mixtures thereof;
ii) substituted aryl, unsubstituted aryl, or mixtures thereof;
iii) substituted aryloxy, unsubstituted aryloxy, or mixtures thereof;
iv) an alkylethyleneoxy unit of the formula:

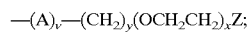

wherein Z is:
a) hydrogen;
b) hydroxyl;
c) $-CO_2H$;
d) $-SO_3^-M^+$;
e) $-OSO_3^-M^+$;
f) $C_1-C_6$ alkoxy;

g) substituted aryl, unsubstituted aryl, or mixtures thereof;
h) substituted aryloxy, unsubstituted aryloxy, or mixtures thereof;
i) alkyleneamino; or mixtures thereof;

A is nitrogen or oxygen, M is a water soluble cation, v is 0 or 1, x is from 0 to 100, y is from 0 to 12;

and mixtures thereof, and D is a unit which increases the efficiency of singlet oxygen production, said unit having the formula

—$L^1$—E or

—$L^1$—B—[$L^2$—E]$_m$ wherein E is an aromatic unit having six carbon atoms, provided said E aromatic unit:
  a) absorbs ultra violet radiation at a wavelength of from about 200 nm to about 400 nm;
  b) has an extinction coefficient of at least about 100; and
  c) has a fluorescence spectrum which overlaps the absorption band of said photosensitizer unit;

B is a branching unit; and $L^1$ and $L^2$ are linking units, provided said linking units when taken together with said B unit comprise a total of at least 20 continuous covalent bonds from said P unit to said E units; m is from 2 to 4.

* * * * *